US006197583B1

(12) United States Patent
Azad et al.

(10) Patent No.: US 6,197,583 B1
(45) Date of Patent: Mar. 6, 2001

(54) THERAPEUTIC COMPOUNDS

(75) Inventors: Ahmed Abdullah Azad; Cyril C Curtain; Alison Louise Greenway; Dale Alan McPhee; Ian MacReadie, all of Melbourne (AU)

(73) Assignees: Biomolecular Research Institute Ltd., Parkville; Macfarlane Burnet Centre for Medical Research Ltd., Fairfield; Commonwealth Scientific and Industrial Research Organisation, Parkville, all of (AU)

( * ) Notice: Subject to any disclaimer, the term of this patent is extended or adjusted under 35 U.S.C. 154(b) by 0 days.

(21) Appl. No.: 09/285,070

(22) Filed: Apr. 20, 1999

Related U.S. Application Data

(62) Division of application No. 08/553,271, filed as application No. PCT/AU94/00254 on May 18, 1994, now Pat. No. 5,962,635.

(30) Foreign Application Priority Data

May 18, 1993 (AU) .................................... PL 8861

(51) Int. Cl.[7] ............................. C12N 5/00; A61K 38/00; C12Q 1/70
(52) U.S. Cl. ......................... 435/339.1; 530/326; 435/5; 435/334
(58) Field of Search ............................ 435/5, 334, 339.1; 530/326

(56) References Cited

U.S. PATENT DOCUMENTS 5,221,610   6/1993   Montagnier et al. .................. 435/7.1

FOREIGN PATENT DOCUMENTS

| 42229/93 | 12/1993 | (AU) . |
| WO89/09227 | 10/1989 | (WO) . |
| WO94/28421 | 12/1994 | (WO) . |

OTHER PUBLICATIONS

Choppin et al., HLA–Binding Regions of HIV–1 Proteins: I. Detection of Seven HLA Binding Regions in the HIV–1 Nef Protein, J. Immunol. 147, 569–574, see Abstract, Jul. 1991.

Delassus, Sylvie, Cheynier, Remi and Wain–Hobson, Simon, Evolution of Human Immunodeficiency Virus Type I, vol. 65, No. 1, 1991 p. 225–231.

(List continued on next page.)

Primary Examiner—Hankyel Park
(74) Attorney, Agent, or Firm—Jacobson, Price, Holman & Stern, PLLC

(57) ABSTRACT

The invention relates to a biologically-active peptide fragment of the Nef protein of human immunodeficiency virus, to pharmaceutical compositions comprising these peptides or biologically-active analogues thereof, to antagonists of the peptides and to pharmaceutical compositions comprising these antagonists, and to therapeutic and screening methods utilizing compounds and compositions of the invention.

3 Claims, 18 Drawing Sheets

OTHER PUBLICATIONS

Ahmad, Nafees, Venkatesan, Sundarorajan, Nef Protein of HIV–1 Is a Transcriptional Repressor, Science, vol.241, pp.1481–1485, 1988.

Fischer, Amanda Infectious Mutants of HTLV–III with Changes in the 3'Region and Markedly Reduced, Science vol.233, pp.655–659, 1986.

Luciw, Paul A., Mutational anaylsis of the human immunodficiency virus, Proc. Natl. Acad. Sci. USA, vol. 84, pp. 1434–1438, 1987.

Luria, Sylvie, Expression of the Type 1 human immunodeficiency virus Nef protein, Proc. Natl. Acad. Sci. vol.88, pp.5326–5330, 1991.

Nature, vol. 330, Nov. 19, 1987, pp. 266–269, B. Guy et al, "HIV F/3'orf encodes a phosphorylated GTP–binding protein resembling . . . ".

International Journal of Peptide and Protein Research, vol. 35, No. 1, Jan. 1990, pp. 63–72, Sabatier et al, "Large Fragments of nef–protein and gp110 envelope glycoprotein from HIV–1".

AIDS, vol. 6, No. 8, Aug 1992, pp. 787–791, L. Poulin et al, "The HIV–1 nef gene product is associated with phophorylation . . . ".

Journal of Virology, vol. 66, No. 9, Sep. 1992, pp. 5256–5264, Blumberg et al, "Human Immunodeficiency Virus type 1 nef . . . ".

Melittin

Net Peptide

FIG. 9A

DOWN-REGULATION OF CD4 AND IL-2R BY Nef 27 BUT NOT Nef 25

Mw (kDa)

DOWN-REGULATION OF CD4 AND IL-2R BY Nef 27 BUT NOT Nef 25

Mw (kDa)

25 ▶

E  F  G  H

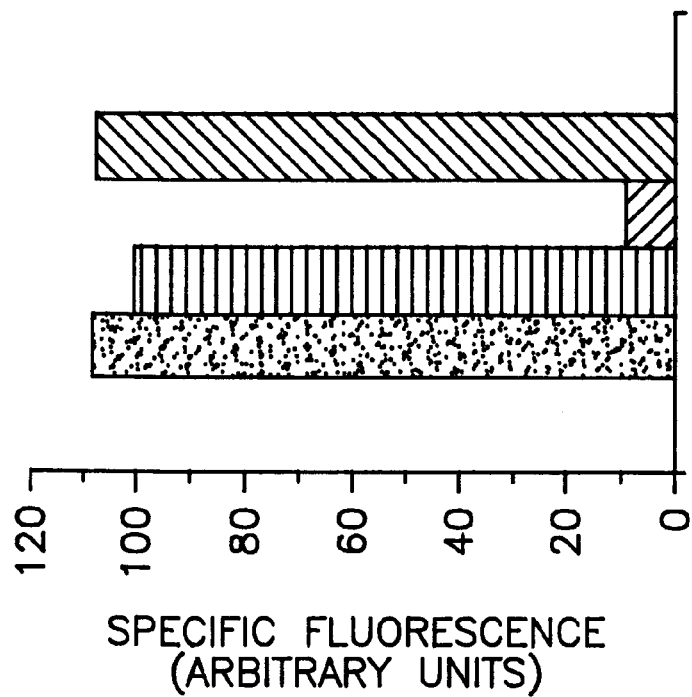
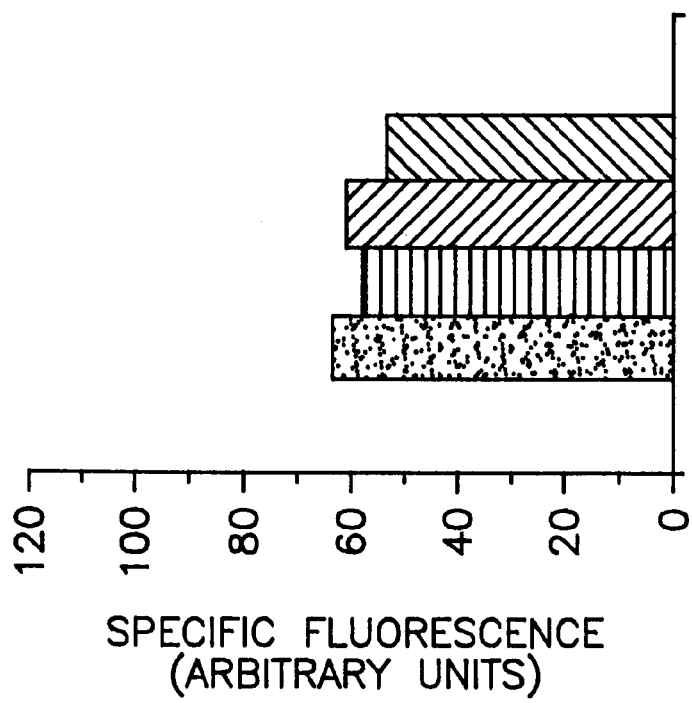

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 21 amino acids
      (B) TYPE: amino acid
      (C) STRANDEDNESS: Not Relevant
      (D) TOPOLOGY: Not Relevant -continued

```
    (ii) MOLECULE TYPE: peptide (iii) HYPOTHETICAL: NO (iv) ANTI-SENSE: NO (v) FRAGMENT TYPE: N-terminal (vi) ORIGINAL SOURCE:
         (A) ORGANISM: Human immunodeficiency virus type 1
         (C) INDIVIDUAL ISOLATE: NEF2-22

(xi) SEQUENCE DESCRIPTION: SEQ ID NO:1:

Gly Gly Lys Trp Ser Lys Ser Ser Val Ile Gly Trp Pro Ala Val Arg
1               5                  10                  15

Glu Arg Met Arg Arg
            20

(2) INFORMATION FOR SEQ ID NO:2:

(i) SEQUENCE CHARACTERISTICS:
         (A) LENGTH: 24 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (iv) ANTI-SENSE: NO (v) FRAGMENT TYPE: N-terminal (vi) ORIGINAL SOURCE:
         (A) ORGANISM: Apis mellifera (xi) SEQUENCE DESCRIPTION: SEQ ID NO:2:

Gly Ile Gly Ala Val Leu Lys Val Leu Thr Thr Gly Leu Pro Ala Leu
1               5                  10                  15

Ile Ser Trp Ile Lys Arg Lys Arg
            20
```

THERAPEUTIC COMPOUNDS

This is a Divisional of application Ser. No. 08/553,271 filed Mar. 6, 1996, now U.S. Pat. No. 5,962,635 which in turn was filed under 35 USC 371 based on PCT international application Number PCT/AU94/00254 filed on May 18, 1994, which in turn was based on Australian application No. PL 8861 filed on May 18, 1993.

This invention relates to a biologically-active peptide fragment of the Nef protein of human immunodeficiency virus, to pharmaceutical compositions comprising these peptides or biologically-active analogues thereof, to antagonists of the peptides and to pharmaceutical compositions comprising these antagonists, and to therapeutic and screening methods utilising compounds and compositions of the invention.

BACKGROUND OF THE INVENTION

Human immunodeficiency virus (HIV-1), the aetiological agent of AIDS, is distinguished by a genomic structure which is more complex than observed with other animal retroviruses. The genome of HIV-1 has been found to encode the major structural proteins, derived from the gag, pol and env genes, and at least seven non-essential auxiliary proteins derived from the tat, rev, nef, vif, vpu, vpr and tev genes (1,2). Several of these proteins have clearly defined functions; for example, it is known that Tat and Rev regulate viral gene expression, while Vif and Vpu are thought to be required for virion morphogenesis and maturation (3,4,5). However, the function of the other auxiliary proteins such as Nef is more ambiguous.

The nef gene product, a 25–30 kDa protein, is modified by N-terminal myristoylation and phosphorylation and is expressed early in infection (6,7). It is associated with cytoplasmic membrane structures in HIV-infected cells. The Nef protein is encoded by a single open reading frame of the virus genome overlapping with the 3' long terminal repeat sequence (LTR; 8,9). While recent studies of Rhesus monkeys infected with simian immunodeficiency virus have suggested an important role for Nef in the maintenance of high virus load and in viral pathogenesis (10), and while prolonged survival in HIV-infected patients is correlated with the absence of Nef, the biological function and mechanism of action of Nef remain controversial. Nef has been reported to be a negative regulator of HIV-1 replication (2,10,11): T cells stably transformed for Nef expression demonstrate a delay in virus multiplication (11). Further reports have suggested that Nef may act to repress transcription from the HIV-1 LTR (12,13,14), such that Nef may act to regulate the positive effects of the viral transactivator, Tat. However, other studies have been unable to confirm the inhibitory effects of Nef on viral transcription or replication in vitro, and indeed in one instance showed that Nef enhances viral replication (15).

We have found that Nef possesses no G-protein activities, using highly purified recombinant Nef protein produced in either *E. coli* or yeast.

The effect of HIV-1 Nef on host-cell function is equally controversial. The major targets for HIV-1 infection are CD4$^+$ T-lymphocytes (16,17). This cell population, most of which constitutes the T-helper cell category, is intimately involved in the host cell response to infection. Specific interactions of the CD4 antigen with invariant determinants of MHC class II molecules on antigen-presenting cells, in conjunction with recognition of peptide antigen by the T-cell receptor (TCR), initiate the events which lead to the expression of the activated T-cell phenotype. Moreover, it has been proposed that CD4 and its associated tyrosine kinase may play an active role in the CD3/TCR activation process (18,19). By use of a vaccinia virus recombinant expressing the nef gene, or the nef gene under control of a murine retrovirus LTR, it has been found that the protein is capable of down-regulating CD4 cell surface expression in CEM T4 cells (20,21). Down-regulation occurred after translation of CD4 mRNA and before expression of mature protein on the cell surface. Furthermore, there is evidence that virally-encoded Nef protein interferes with a signal emanating from the TCR complex that induces IL-2 gene transcription (22). Hence, rather than affecting viral replication, Nef may act to alter the normal host cell response to infection by impairing signal transduction pathways. However, interpretation of these results requires caution because of findings that cells transduced with the same vector, but with no functional nef gene, also exhibited reduced expression of surface CD4 (23), while the effect of Nef upon IL-2 gene transcription remains to be substantiated.

The mechanisms of activation of T cells and of their stimulation with IL-2 are not yet completely understood. However, it is known that stimulation of activated T cells with IL-2 leads to a rapid, transient increase in the catalytic activity of the enzyme p56$^{lck}$, a member of the protein tyrosine kinase (PTK) group of enzymes, accompanied by the phosphorylation of this PTK on multiple serine residues (43). A growing body of evidence suggests that tyrosine and serine/threonine protein kinases, and in particular p56$^{lck}$, which are known to be associated with the β chains of IL-2 receptor and of CD4, may be involved in IL-2-dependent proliferative signals (18,44).

In order conclusively to determine possible functions of the HIV-1 Nef protein, we have obtained Nef protein in a highly purified form, and have studied its effects on cellular function. Nef 27 and Nef 25, translated from the first and second initiation codons of the nef gene of HIV-1 clone pNL4.3 respectively, were overproduced in *E. coli* and purified to homogeneity.

We have also synthesised peptides corresponding to amino acids 2–19 and 2–22 of the N-terminal sequence of Nef. Using these purified proteins and peptides, we have demonstrated that Nef has membrane-perturbing properties, in that it is capable of fusing small unilamellar phospholipid vesicles and of inducing non-lamellar phases in lipid bilayers. These properties appear to reside in the 21 residue N-terminal sequence of Nef, which has considerable homologies across all strains of HIV with the sequence of the membrane-perturbing honey bee venom peptide, melittin.

We have used an electric field electroporation technique termed Baekonization to introduce the highly purified Nef 27 or Nef 25 into various CD4$^+$ T-cell lines and phytohaemagglutinin (PHA)-activated peripheral blood mononuclear cells (PBMC), in order to investigate the effect of these proteins on CD4 cell surface expression and expression of IL-2 receptor (IL-2 R). We have found that the T-cell lines MT-2, CEM and Jurkat, and PHA-activated PBMC, containing Nef 27 after electroporation showed significantly reduced expression of surface CD4. Additionally, MT-2 cells and PBMC containing Nef 27 also demonstrate severely reduced expression of IL-2 R, constitutively in the case of MT-2 cells or after stimulation with PHA in PBMC. In direct contrast, the T-cell lines and PBMC which contain Nef 25 after electroporation expressed unaltered levels of surface CD4 and IL-2 R.

As well as identifying the active region of the Nef protein, we have found that Nef 27 inhibits the proliferative response of PHA-activated PBMC in response to recombinant IL-2, and that Nef 27 is able to inhibit the phosphorylation of $p56^{lck}$ in PBMC which is induced by IL-2 stimulation, while Nef 25 is not. We have been able to demonstrate an interaction between Nef and $p56^{lck}$, which may be involved in the inhibition of cell proliferation and IL-2-dependent phosphorylation of $p56^{lck}$ by Nef 27.

SUMMARY OF THE INVENTION

According to a first aspect, the invention provides an immunosuppressive peptide comprising the $Nef_{2-19}$ peptide or an immunosuppressive analogue thereof, wherein the N-terminal sequence of said peptide comprises an immunosuppressive region of $Nef_{2-19}$.

According to a second aspect, the invention provides a pharmaceutical composition comprising as active component the $Nef_{2-19}$ peptide, or an immunosuppressive analogue thereof, together with a pharmaceutically-acceptable carrier. It is considered that such compositions will be useful as immunosuppressants. It will be clearly understood that the term "analogue" includes fragments or extensions of the $Nef_{2-19}$ peptide.

The invention also provides a method of suppression of an immune response or of symptoms of autoimmune disease, comprising the step of administering to a subject in need of such treatment an effective amount of $Nef_{2-19}$ peptide or an analogue thereof, or a composition comprising said peptide or analogue.

In both these aspects, the peptide or analogue thereof may be linked either to an extension along the N-terminal sequence of Nef, or to a sequence of Nef which is not adjacent to $Nef_{2-19}$ or $Nef_{2-22}$.

In a third aspect, the invention provides an antagonist of the $Nef_{2-19}$ peptide, which has the ability to inhibit one or more activities selected from the group consisting of Nef 27- or $Nef_{2-19}$ peptide-mediate membrane perturbation, down-regulation of CD4, and down-regulation of IL-2 receptor. It is considered that such antagonists will be useful as therapeutic agents for treatment of HIV infection, and as stimulators of immune responses.

The invention also encompasses a pharmaceutical composition comprising as active component an antagonist of $Nef_{2-19}$ peptide as defined above, together with a pharmaceutically-acceptable carrier.

The invention further provides a method of treatment of HIV infection, comprising the step of administering to a subject in need of such treatment an effective amount of an antagonist of $Nef_{2-19}$ peptide as defined herein, thereby to prevent progression of HIV infection to symptomatic AIDS, or to alleviate the symptoms of AIDS.

In a fourth aspect, the invention provides a method of screening compounds for activity as analogues or antagonists of $Nef_{2-19}$ peptide, comprising measuring the effectiveness of a test compound in an assay of a biological activity of Nef 2–19 peptide selected from the group consisting of membrane perturbation, down-regulation of CD4 expression, and down-regulation of IL-2 receptor expression, as herein described.

In two alternative preferred embodiments of this aspect of the invention, the screening method is quantitative, and utilises either binding of Nef to $p56^{lck}$ or inhibition by Nef or phosphorylation of $p56^{lck}$. Such quantitative methods readily adaptable to rapid, large scale screening of test compounds for their ability to promote or disrupt these functions of Nef.

Because there is homology between the peptide sequences of $Nef_{2-19}$ peptide and bee venom melittin, it is considered that this and other venom peptides, such as spider venom peptides, would provide suitable starting materials for design of inhibitors of activity of the $Nef_{2-19}$ peptide.

The person skilled in the art will recognise that specific antibody, preferably monoclonal antibody, directed against $Nef_{2-19}$ peptide, and antisense RNA or triple-stranded DNA which prevents expression either of the $Nef_{2-19}$ peptide moiety or of the full-length Nef sequence, provide methods of inhibition of the activity of the $Nef_{2-19}$ peptide, and consequently are within the scope of this invention. Methods for production of monoclonal antibodies against a given peptide sequence, and methods for inducing antisense RNA production or triple-stranded DNA in a target cell, are well known in the art. For example, a nef gene in which the N-terminus has been replaced by an inhibitory antisense sequence or by a sequence which encodes an inhibitory peptide could be used for gene therapy of AIDS.

It will further be clearly understood that recombinant, synthetic, and naturally-derived Nef 27, Nef 25, $Nef_{2-19}$ and $Nef_{1-22}$ peptides, and fragments and analogues thereof with or without N-terminal myristoylation are all within the scope of this invention.

While the description herein relates specifically to Nef protein or HIV-1, HIV-2 also possesses a Nef protein, and the invention is equally applicable to the Nef protein and the equivalent of $Nef_{2-19}$ peptide derived from HIV-2. Similarly, while the description refers specifically to the $Nef_{2-19}$ peptide, the $Nef_{2-22}$ peptide also forms part of the invention.

DETAILED DESCRIPTION OF THE INVENTION

The invention will now be described in detail by way of reference only to the following non-limiting examples, and to the drawings, in which:

FIG. 1 summarises the scheme employed for cloning and expression of HIV-1 nef genes in *E. coli,* yeast, and baculovirus;

FIG. 2 shows plots of hydrophobic moment against hydrophobicity;

FIG. 3 compare helical wheel diagrams illustrating Nef and melittin, showing the distribution of polar and hydrophobic residues around the α-helices of the two peptides;

Figure 10:
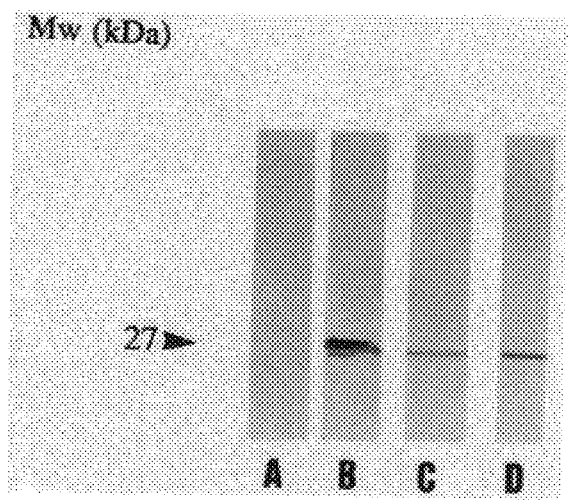

FIG. 9 shows immunoblots of recombinant Nef 27 and Nef 25 reacted with affinity purified anti-$Nef_{(15-27)}$. Varying amount of recombinant Nef protein (lanes A and H:3.0 μmol; lanes B and G:1.5 μmol; lanes C and F:0.5 μmol and lanes D and E:0.15 μmol) were used to determine the amount of protein detectable by the antibodies in western immunoblotting. Nef 27 is in lanes A–D and Nef 25 is in lanes E–H. Strong bands specific for Nef 27 or Nef 25 were still observed when 0.15 μmol of protein was tested;

FIG. 10 illustrates detection of Nef protein in electroporated MT-2 cells by immunoblotting. Immunoblots of cell lysates prepared from MT-2 cells were electroporated as follows:
a) mock-electroporation,
b) electroporated with recombinant Nef 27 (1.0 μmol),
c) electroporated with Nef 25 (1.0 μmol),
d) recombinant Nef 25 alone (1.0 μmol).
All samples were immunoblotted with anti-$Nef_{14-27}$;

FIG. 11 shows expression of cell surface-located CD4 in MT-2 cells (A) and PHA-stimulated peripheral blood mononuclear cells (B), and of IL-2 R in MT-2 cells (C) and PHA-stimulated PBMC (D). Cells were mock-electroporated (1) or electroporated with either BSA; 1.0 μmol (2), Nef 27; 1.0 μmol (3), or Nef 25; 1.0 μmol (4), and incubated at 37° C. for 24 h. Cells were then reacted with anti-CD4, anti-CD25, denoted by the striped bars, or the appropriate isotype control, denoted by the black bars, and analysed by flow cytometry. Mean fluorescence intensities of positive cells are indicated;

FIG. 12 shows expression of cell surface-located transferrin receptor (TFR) (A) or IL-2 R (B) in MT-2 cells. Cells were electroporated with either Nef 27; 1.0 μmol , Nef 25; 1.0 μmol , BSA; 1.0 μmol  or mock electroporated , and incubated at 37° C. for 24 h. Cell surface expression of TFR on MT-2 cells was stable, even after electroporation of cells with HIV-1 Nef 27;

FIG. 13 shows silver staining of polyacrylamide gel electrophoresed cellular protein precipitates.
a) Precipitates prepared from MT-2 cell lysates after reaction with TBS (track 1), GST (track 2) or GST-Nef 27 (track 3) followed by glutathione-Sepharose.
b) Precipitates prepared form PHA-activated PBMC lysates after reaction with TBS (track 3), GST (track 4) or GST-Nef 27 (track 5) followed by glutathione-Sepharose. Track 1 represents GST protein (2 μg), track 2 represents GST-Nef 27 protein (2 μg).
c) Precipitates prepared from PHA-activated PBMS lysates after reaction with TBS (track 5), GST (track 6) or GST-Nef 27 (track 7) followed by glutathione-Sepharose. Track 1 represents low molecular weight markers, track 2 represents GST protein (2 μg), track 3 represents GST-Nef 25 (2 μg).

FIG. 14 shows Western immunoblotting of cellular protein precipitates.
a) Precipitates prepared from MT-2 cells after reaction with TBS (track 1), GST (track 2) and GST-Nef 27 (track 3). Anti-$p56^{lck}$ was used as the primary antibody.
b) Precipitates prepared from PHA-activated PBMC after reaction with TBS (track 4), GST (track 3) and GST-Nef 27 (track 2). Anti-$p56^{lck}$ was used as the primary antibody. Track 1 represents low molecular weight markers.

Figure 15:
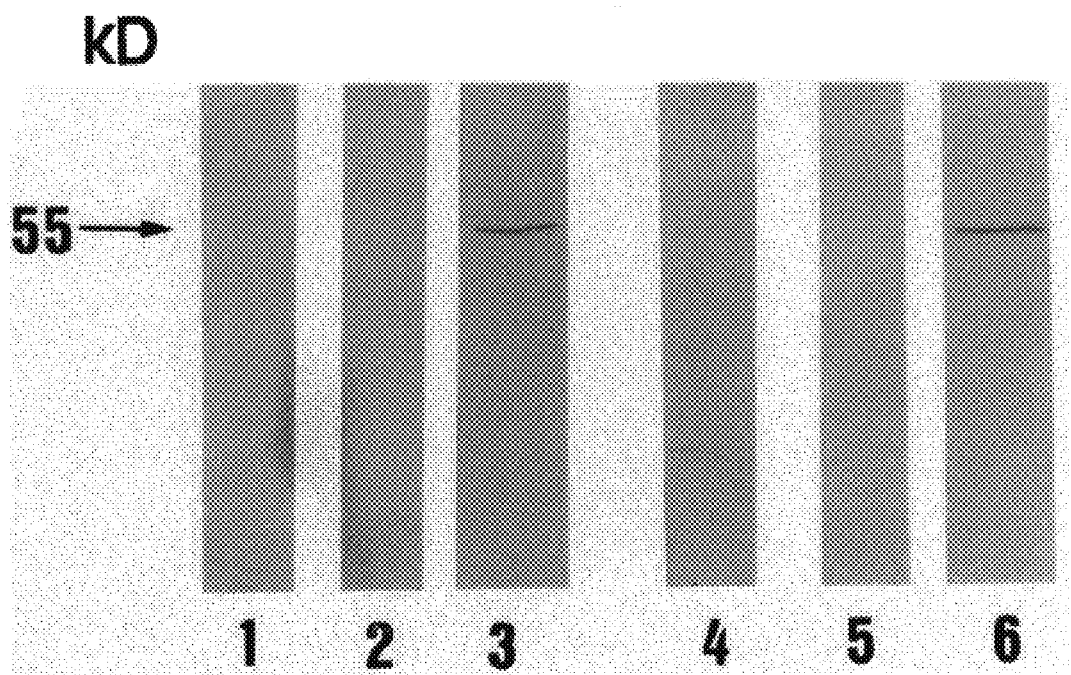

FIG. 15 shows Western immunoblotting of cellular protein precipitates prepared from PHA-activated MT-2 cells after reaction with TBS (track 1), GST (track 2) and GST-Nef 27 (track 3) or PHA-activated PBMC after reaction with TBS (track 4), GST (track 5) and GST-Nef 27 (track 6) as described below. Anti-CD4 was used as the primary antibody.

Figure 16:
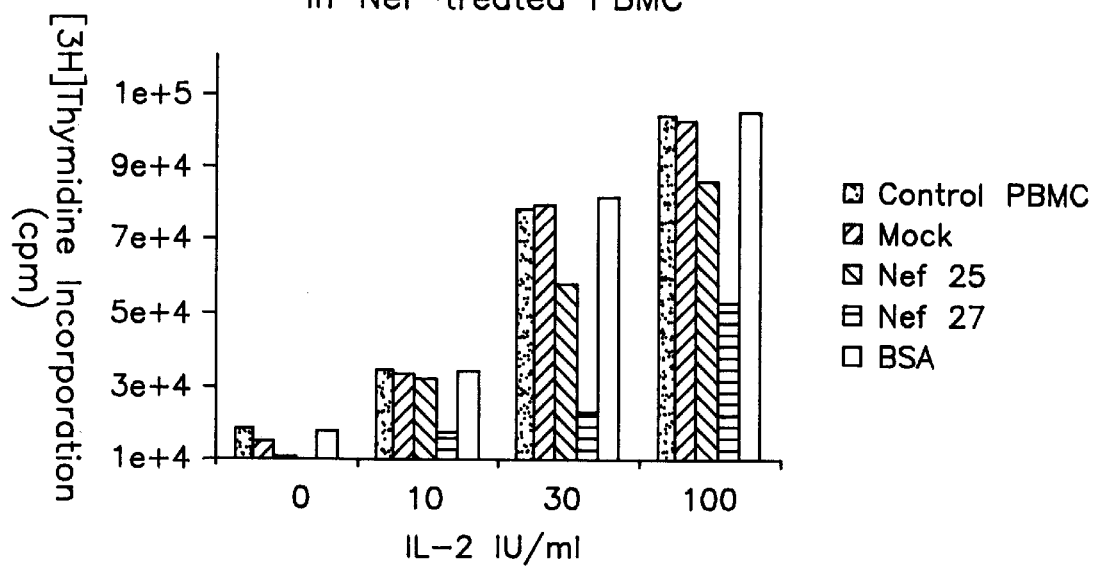

FIG. 16 illustrates the proliferative response to IL-2 (0, 10, 30 and 100 IU/ml) of PHA-activated PBMC mock-electroporated or electroporated with Nef 25, Nef 27 or BSA, using [$^{3}H$]-thimidine incorporation as the index. PHA-activated PBMC which did not undergo the electroporation process were included as controls. Results represent mean ±S.D. for three experiments.

Figure 17:
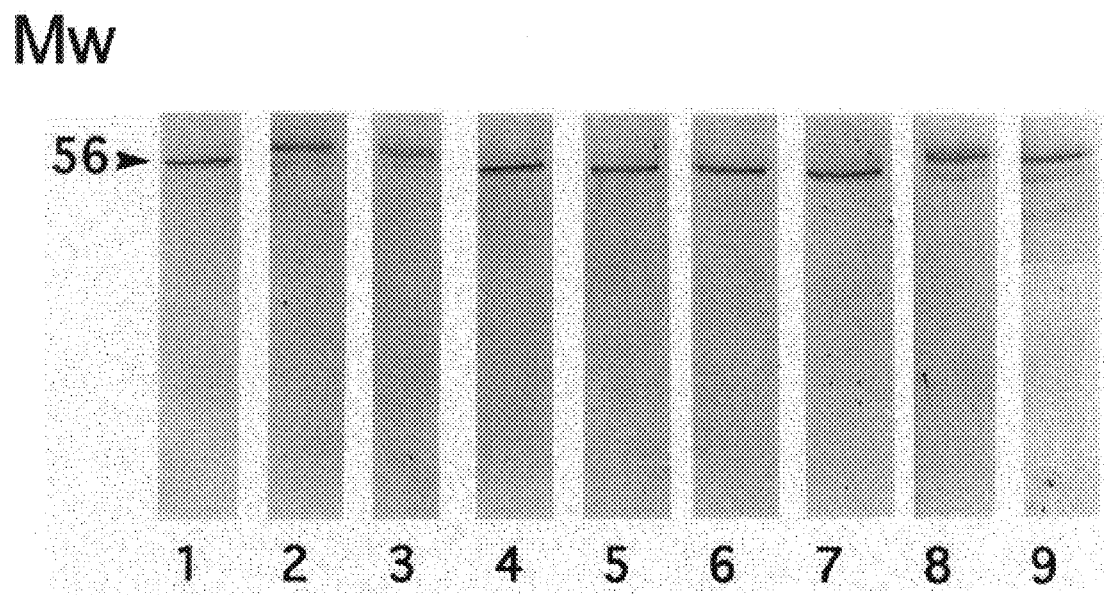

FIG. 17 shows Western immunoblotting of Nef-treated PBMC lysate with anti-$p56^{lck}$. PHA-activated PBMC mock electroporated (tracks 1, 2 and 3), electroporated with Nef 27 (tracks 4, 5 and 6), or electroporated with Nef 25 (tracks 7, 8 and 9) were treated with IL-2 (1000 U) for 0 min (tracks 1, 4 and 7), 15 min (tracks 2, 5 and 8) or 30 min (tracks 3, 6 and 9), and electrophoresed in a 13% polyacrylamide gel. After transfer to Hybond-C Super nitrocellulose the filters were reacted with anti-$p56^{lck}$ as described below.

Figure 18:
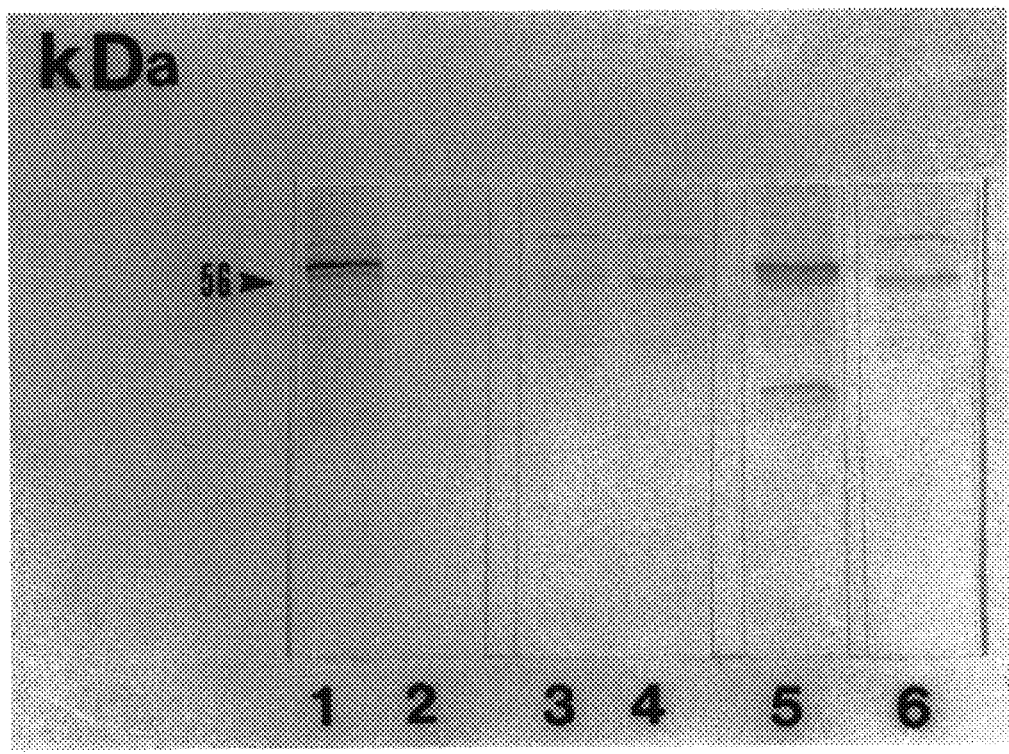

FIG. 18 shows Western immunoblotting of Nef-treated PBMC lysates with anti-$p56^{lck}$ before and after PMA stimulation.
PBMC mock electrophorated (tracks 1 and 2), electroporated with Nef 27 (tracks 3 and 4) or electroporated with Nef 25 (tracks 5 and 6) were treated with PMA (20 ng/ml; tracks 1, 3 and 5) or incubated in medium alone for 2 h at 37° C. Cell lysates were electrophoresed, transferred to Hybond-C Super nitrocellulose and subsequently probed with anti-$p56^{lck}$.

Figure 19:
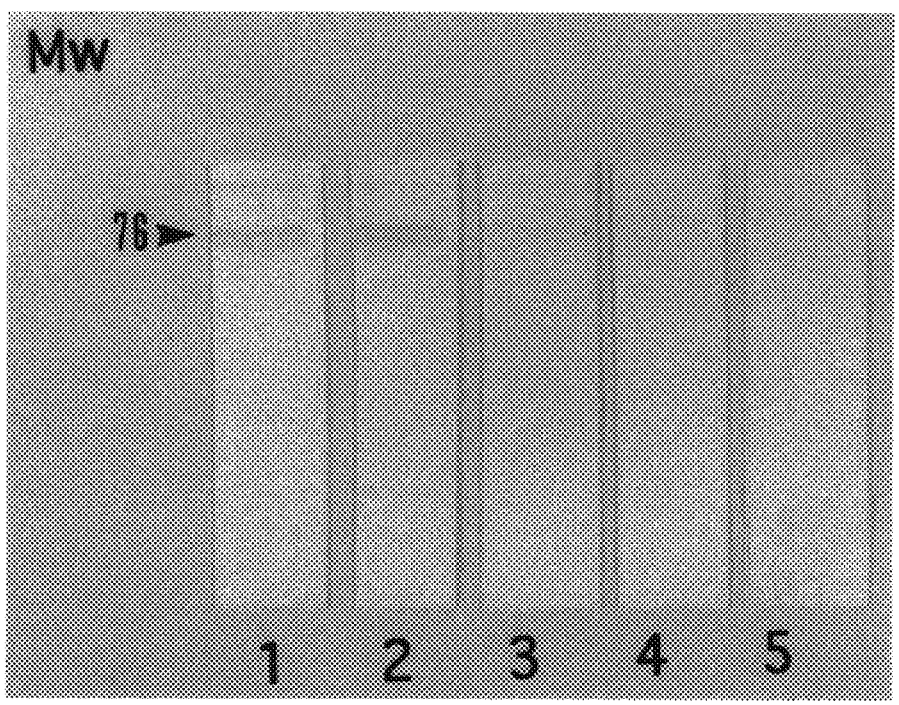

FIG. 19 shows levels of nucleoprotein c-myb in Nef-treated MT-2 cells as detected by western immunoblotting.
MT-2 cells electroporated with Nef 27 (tracks 4 and 5), Nef 25 (track 3), mock-electroporated cells (track 2) or control MT-2 cells (track 1) were lysed, electrophoresed, transferred to Hybond-C Super nitrocellulose and reacted with anti-c-myb.

MATERIALS AND METHODS

Reagents: Dipalmitoyl phosphatidyl choline (DPPC) was purchased from Sigma, St. Louis, Mo. and the spin-labelled phospholipids (1-Palmitoyl-2-(16-doxyl stearoyl) phosphatidyl choline (16 PC-SL), 1-Palmitoyl-2-(12-doxyl stearoyl) phosphatidyl choline (12 PC-SL), and 1-Palmitoyl-2-(5-doxyl stearoyl) phosphatidyl choline (5 PC-SL) were purchased from Avanti PolarLipids, Pelham, Al. Tempo choline chloride⁻ (TCC), the fluorochromes octadecyl rhodamine, 1-aminonaphthaline-3,6,8-trisulphonic acid (ANTS) and the fluorescence quencher N,N'-p-xylenebis-(pyridinium bromide) (DPX) were purchased from Molecular Probes, Junction City, Oreg.

Nef 27 and Nef 25: These proteins were expressed in *E. coli* and purified as described in Azad et al (54). This method enables the production of tens of milligrams of Nef 27 and Nef 25, amounts which permit biological and structural studies to be undertaken.

Figure 1:
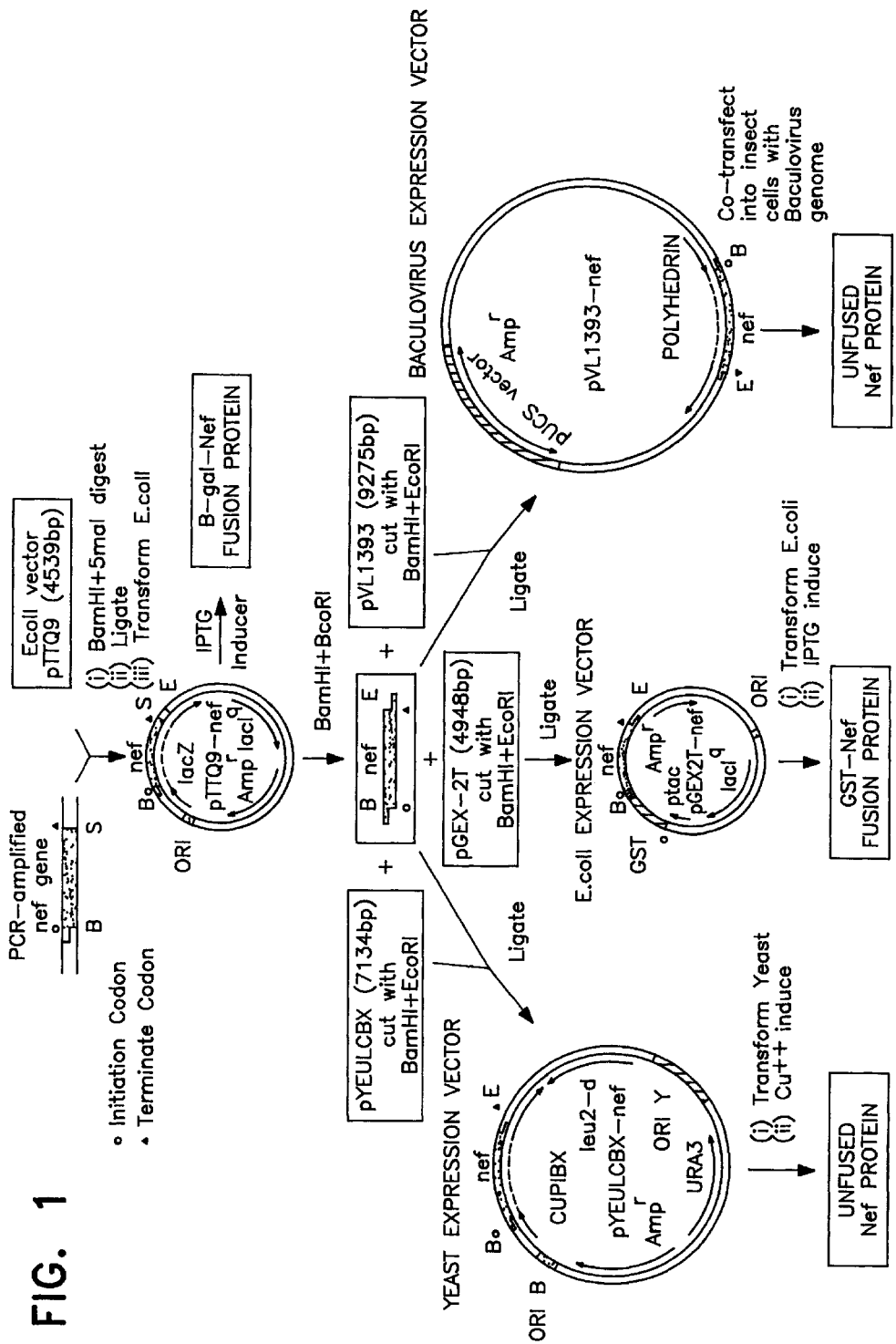

Sequences encoding Nef 27 and Nef 25 were amplified by PCR from the HIV-1 infectious clone pNL4.3 (Adachi et al, J. Virol. 1986 59 284–291) and subcloned directly into *E. coli,* yeast and baculovirus expression vectors. The scheme employed is summarised in FIG. 1. The yeast and baculovirus-derived Nef had native N-termini, but the expression levels were low. The expression level of the *E. coli*-derived glutathione (GST)-Nef fusion proteins was very high, and a major portion of the expression products was soluble. Large-scale production of *E. coli*-derived Nef 27 and Nef 25 was carried out by growing recombinant cells in a fermenter under fed-batch conditions. The soluble GST-Nef fusion proteins were affinity purified on glutathione-Sepharose. After thrombin cleavage at the fusion junction, the GST was selectively removed by binding it to glutathione-Sepharose. Under conditions of large-scale production Nef 27 was always contaminated with a slightly smaller N-terminal cleavage product, and the two could be resolved by selective binding of intact Nef 27 to a Reactive-Red 120 dye ligand. A final gel filtration step was sometimes necessary to remove traces of contaminating bacterial proteins. After purification Nef 27 and Nef 25 had the expected N-terminal sequences, and appeared as single monomeric bands on reducing SDS-PAGE and on gel filtration. Under non-reducing conditions both Nef 27 and Nef 25 existed as a mixture of monomers and dimers. The highly purified Nef proteins had no G-protein activities; neither Nef 27 nor Nef 25 had detectable GTP or autophosphorylation activity. Although both proteins showed appreciable GTP binding when compared to bovine serum albumin, chymotrypsin or lysozyme, the level of binding was insignificant compared to that shown by $p21^{ras}$.

Peptide synthesis: Peptides corresponding to the 2nd to 19th and 2nd to 22nd residues of the amino-terminal sequence of Nef were synthesised on an Applied Biosystems peptide synthesiser, using the standard Merrifield solid-phase technique in which the α-amino groups of the amino acids were protected by acid-labile Boc groups. The sequences from the NL4.3 strain of HIV-1 were:

```
2  Gly-Gly-Lys-Trp-Ser-Lys-Ser-Ser-Val-
Ile-Gly-Trp-Pro-Ala-     19    22 Val-Arg-
       Glu-Arg-(Met-Arg-Arg).
```

Amino acid 1 is Met, which is cleaved in vivo in eukaryotic cells.

The serine side chains were protected by benzyl groups and arginine side chains by mesitylene-2-sulphonyl groups. Couplings were achieved by using a 2-molar excess of the asymmetric anhydride of each amino acid, except for arginine, which was coupled using a 4-molar excess of the butanol ester. The completed peptide was cleaved from the resin using the low trifluoromethane sulphonic acid/high hydrofluoric acid technique which yielded the peptide from the 4-methylbenzylbenzhydryl amine resin. The peptide was purified by HPLC on a C4 Vydac column.

Small unilamellar phospholipid vesicles (SUV) were prepared by hydrating dried phospholipids in 0.05 M Tris-HCl buffer; pH 7.3, to a final concentration of 50 mM and sonicating under nitrogen at 35° C. until the suspension was no longer turbid, followed by ultracentrifugation to remove larger vesicles and any titanium particles from the sonicator tip. The spin-labelled phospholipids were incorporated into the vesicles by mixing them with the phospholipid in excess 70/30 chloroform-methanol at the desired spin label/lipid ratio. The mixture was dried under a stream of nitrogen and then kept under vacuum for 24 hr to ensure thorough removal of solvent. The mixture was then hydrated in the desired buffer and sonicated as above.

Ultraviolet fluorescence studies: Fluorescence spectra of the tryptophan residues in the Nef peptide were recorded with a Perkin Elmer MPF3 fluorescence spectrophotometer using an excitation wavelength of 290 nm.

Light-scattering of SUV in the presence and absence of Nef peptide, Nef 27 and Nef 25 was measured using an Hitachi-Perkin Elmer M35 spectrofluorimeter with the excitation and emission wavelengths both set at 560 nm. A relative value of scattering S was obtained from the equation $S=E_c/E_t$, where $E_c$ is the emission due to right-angle scattering of incident radiation by the control SUV and $E_t$ is the emission from SUV to which the proteins and peptides had been added. The concentration of SUV corresponded to 35–50 μg of lipid/ml.

NMR—$^{31}$P NMR spectra of SUV were acquired on a Bruker AMX600 spectrometer at 81 MHz, using standard pulse sequences.

Prediction of peptide secondary structure was carried out using the Chou-Fasman algorithm using an extended data base of 64 proteins, the Schiffer/Edmundson α-helical wheel and the hydrophobic moment program of Eisenberg and Wesson.

Molecular modelling was carried out using the Biosym Insight II and Discover packages on a Silicon Graphics Iris workstation.

Cells and cell culture: Peripheral blood was obtained from five HIV-1 sero-negative volunteers and mononuclear cells prepared by centrifugation on a Ficoll/Hypaque density gradient using a conventional method (24). Peripheral blood mononuclear cells (PBMC) were stimulated with phytohemagglutinin (PHA; 10 μg/10⁶ cells) for up to 72 h at 37° C., and cultured in RPMI 1640 medium supplemented as described below. The CD4⁺ T-cell lines MT-2 (kindly provided by Dr. Y. Hinuma, Institute for Virus Research, Kyoto University, Kyoto, Japan), CEM and Jurkat (both from ATCC) were grown in RPMI 1640 medium supplemented with 10% (vol/vol) foetal calf serum, 25 μg/ml glutamine, penicillin (100 IU/ml) and streptomycin (100 μg/ml) in a 5% $CO_2$ atmosphere at 37° C.

MT-2 cells were harvested from culture during mid-exponential growth and adsorbed with HIV-1 isolate 228200 or HTLV-IIIb for 2 h at 37° C. with agitation. After this incubation period the cells were resuspended in supplemented RPMI 1640, and incubated at 37° C. for 3 to 4 days. MT-2 cells and Jurkat cells were also harvested from culture during mid-exponential growth and prepared for electroporation.

Antipeptide Antisera: Antibodies specific for HIV-1 Nef were raised against a peptide, synthesised as described previously (25), corresponding to the amino acid residues 15–27 (AVRERMRRAEPAA) of Nef encoded by the HIV-1 clone pNL4.3. The peptide was conjugated to keyhole limpet haemocyanin (KLH; Calbiochem, Behring Diagnostics, CA) via glutaraldehyde and this complex was used to immunise sheep (0.5 mg peptide conjugate/sheep). Antibodies to the peptide were purified by affinity chromatography. Reactivity of the antibodies with recombinant HIV-1 Nef 25 and 27 was demonstrated by immunoblotting.

Monoclonal antibodies (mAbs) reactive against an epitope in the carboxyl terminus of the full length Nef protein (AE6 and AG11; National Institute of Allergy and Infectious Disease AIDS Research and Reference Reagent Programme and Anti-Nef mAb; ABT, Maryland, U.S.A.) or reactive with an epitope in the amino terminal part of Nef (NEF2-B2; National Institute of Allergy and Infectious Disease AIDS Research and Reference Reagent Programme) and anti-Nef mAb raised against a synthetic peptide corresponding to amino acid residues 15–27 of HIV-1, HTLV-IIIb Nef; (New England Nuclear Division, Du Pont, U.S.A.) were used in the various assays described below.

EXAMPLE 1

Theoretical Conformation Studies

Figure 2A:
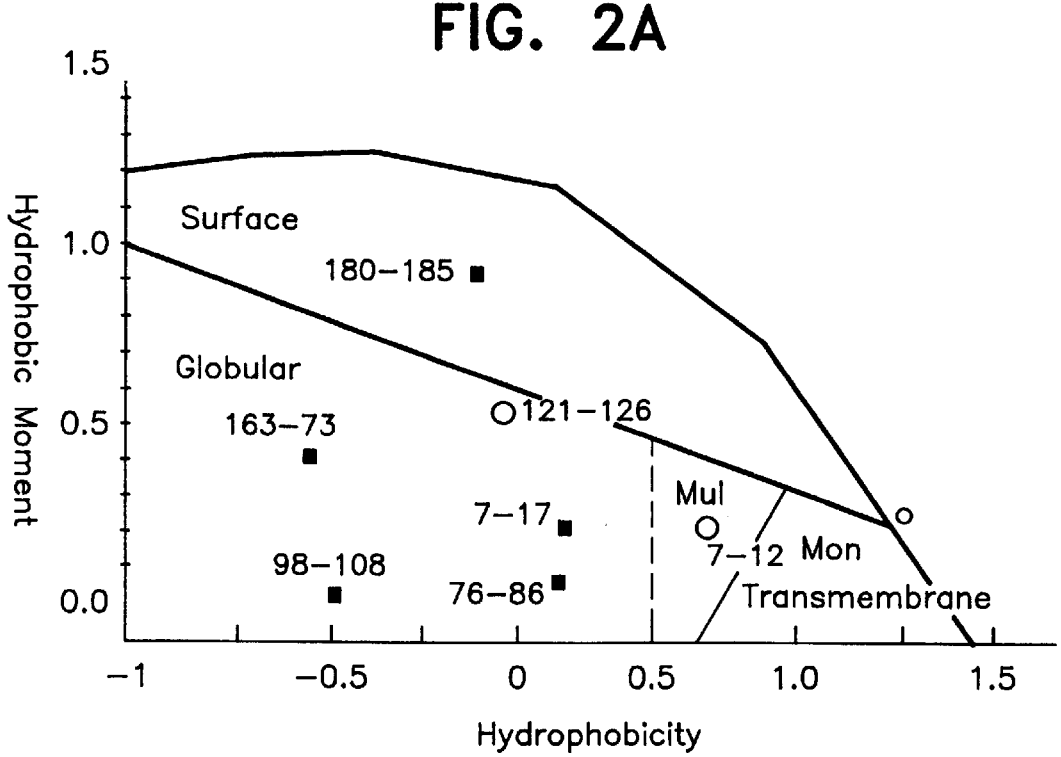
Figure 2B:
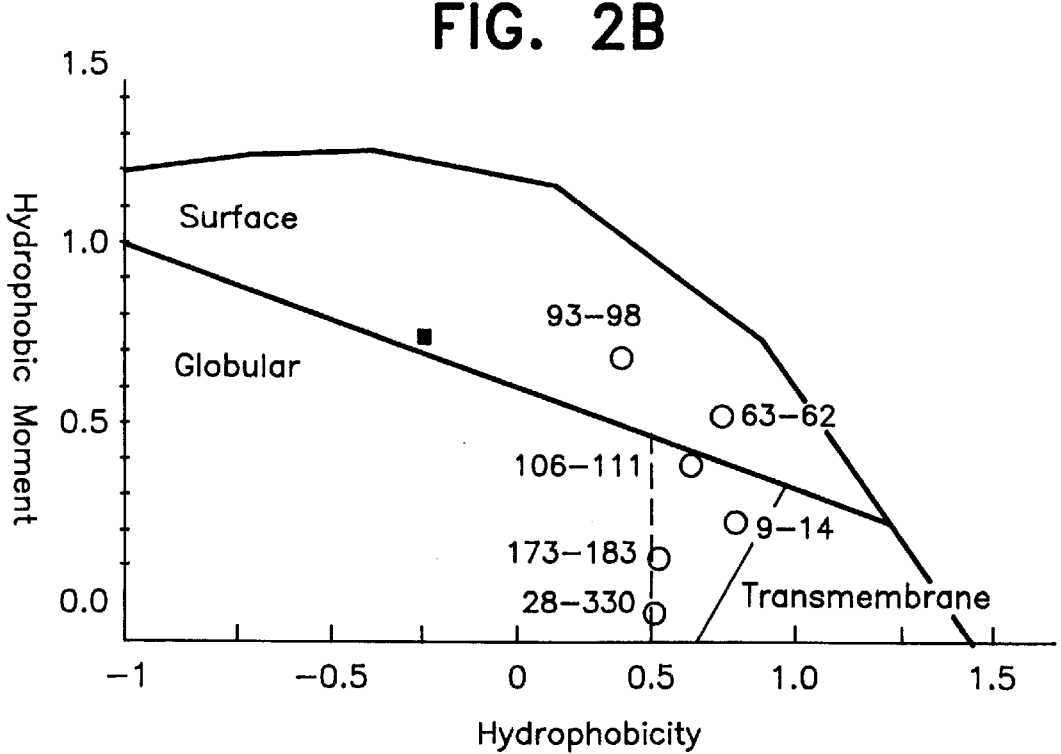
Figure 3B:
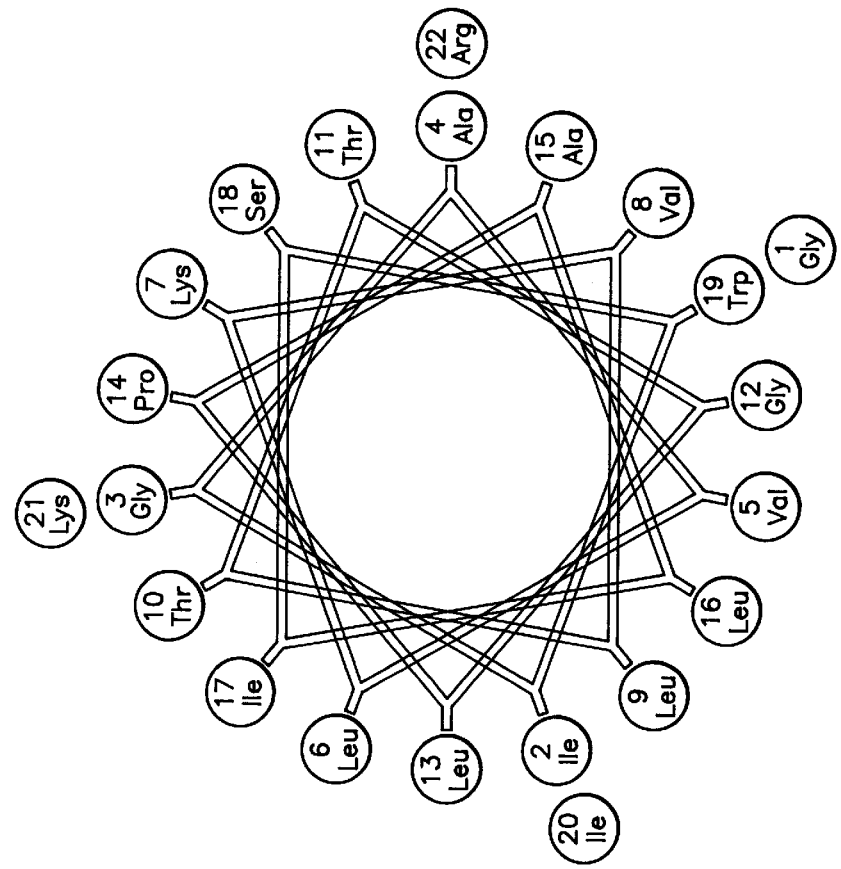
Figure 3A:
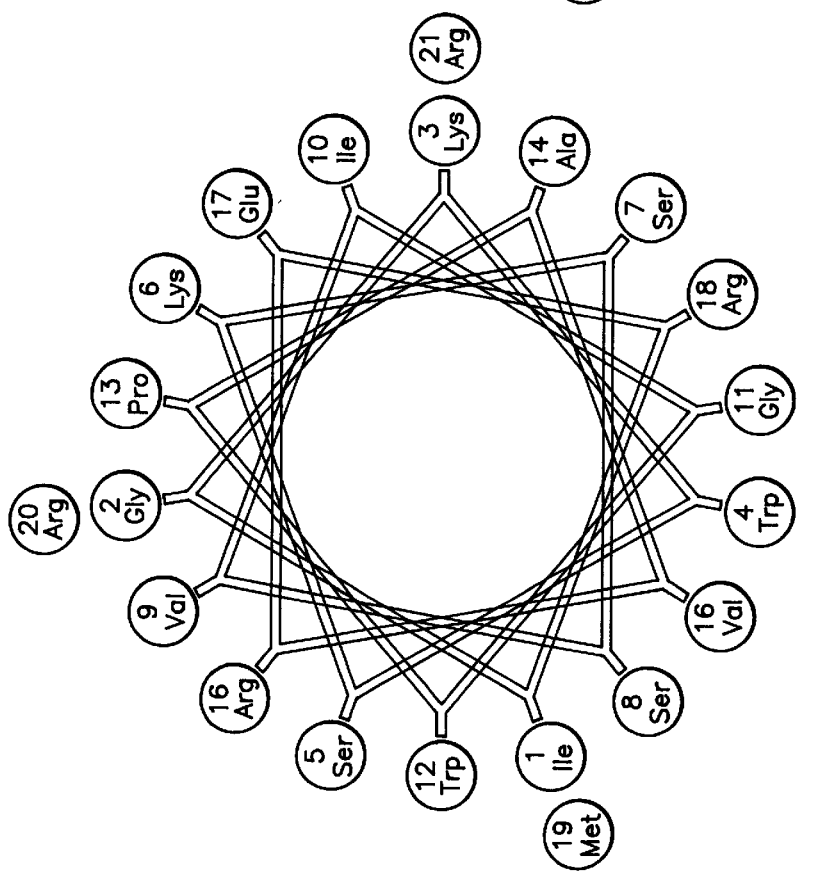

Theoretical calculations were carried out to assess the ability of the Nef peptide to assume a defined secondary structure, such as α-helix or β-strand. Chou-Fasman analysis suggested a low probability of α-helix formation in aqueous solution, and hydrophobic moment plots suggested that the peptide was close to the boundary between surface seeking and "globular" behavious. Plots of hydrophobic moment against hydrophobicity are given in FIG. 2. FIG. 2A was plotted using a 6 residue 'window' and FIG. 2B was plotted using a 4 residue 'window'. It was considered possible that, like melitting, the Nef peptide might form an α-helix in the appropriate environment, such as the interface between a lipid bilayer and aqueous medium. Schiffer-Edmundson diagrams for both peptides are given in FIG. 3. It can be seen that the Nef peptide has a considerably smaller arc than does melittin of hydrophobic residues which could interact with the hydrocarbon region of a lipid bilayer.

EXAMPLE 2

Molecular Modelling

The N-terminal sequences of Nef and of melittin are compared in Table 1.

TABLE 1

Sequence similarity between N-terminus of Nef and Bee Venom Mellitin

| | 2 | | | | | | | | | | | 19 | 22 | | | | |
|---|---|---|---|---|---|---|---|---|---|---|---|---|---|---|---|---|---|
| | G | K | S | S | S | V | I | | | R | E | R | | | | Nef (NL 4-3) |
| G | I | A | L | V | L | T | T | | | I | S | W | | K | R | 2 2 | Mellitin |
| 1 | | | | | | | | | | | | | | | | 26 | |

Figure 4A:
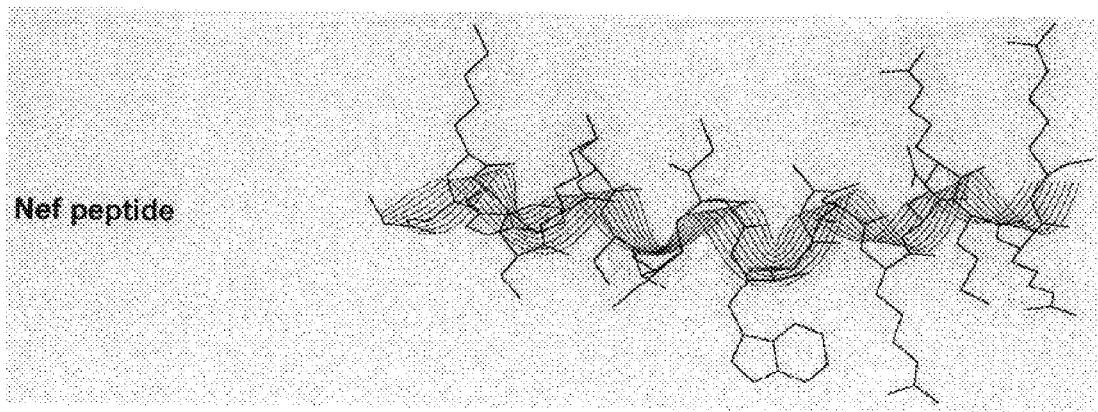
FIG. 4 represents energy-minimised structures for a representative Nef peptide sequence from HIV (A) and for melittin (B)
Figure 4B:
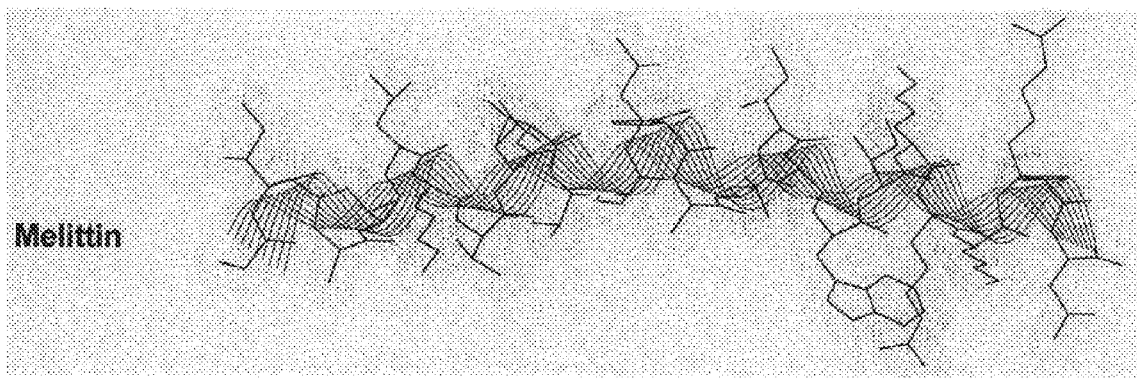

An energy-minimised structure of a representative Nef peptide representing several different strains of Nef is compared with the structure of melittin in FIG. 4. A set of coordinates for the structure of the latter is available from NMR studies. The Nef structure was assembled applying α-helical constraints, and energy minimised using the Discover program. Both the structures are presented with the hydrophobic residues facing downwards. Like melittin, the Nef peptide has a proline residue, approximately half-way along the sequence, which produces a characteristic kink in the helix. A striking difference between melittin and Nef is the fact that while the hydrophobic residues of the former lie along the concave face of the helix, those of the latter lie along its convex face.

EXAMPLE 3

Figure 5:
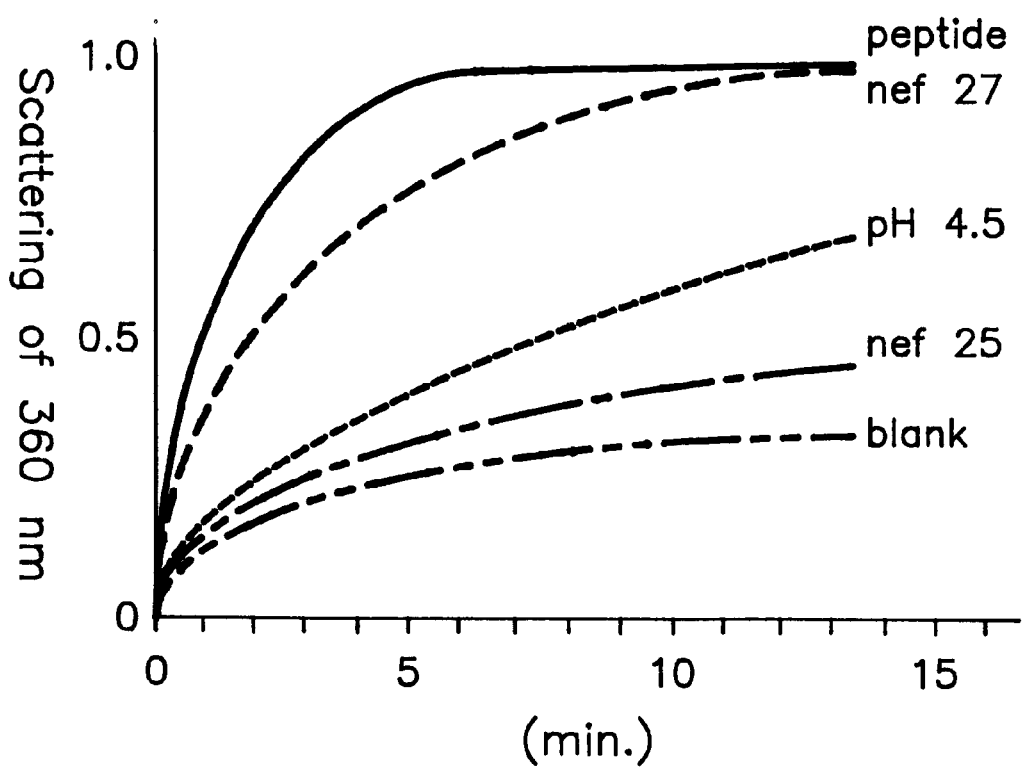
FIG. 5 shows light-scattering of small unilamellar phospholipid vesicles (SUV) in the presence of $Nef_{2-19}$ peptide, Nef 27 and Nef 25.

Light-Scattering Studies On The Interaction Of Nef 27, Nef 25 And Nef Peptide With SUV Nef 27 and Nef peptide caused a rapid increase in light-scattering of SUV, as shown in FIG. 5. Nef 25 increased scattering to a considerably lesser extent. The increase in light scattering indicates aggregation of the vesicles, probably due to fusion.

EXAMPLE 4

NMR Studies

Figure 6:
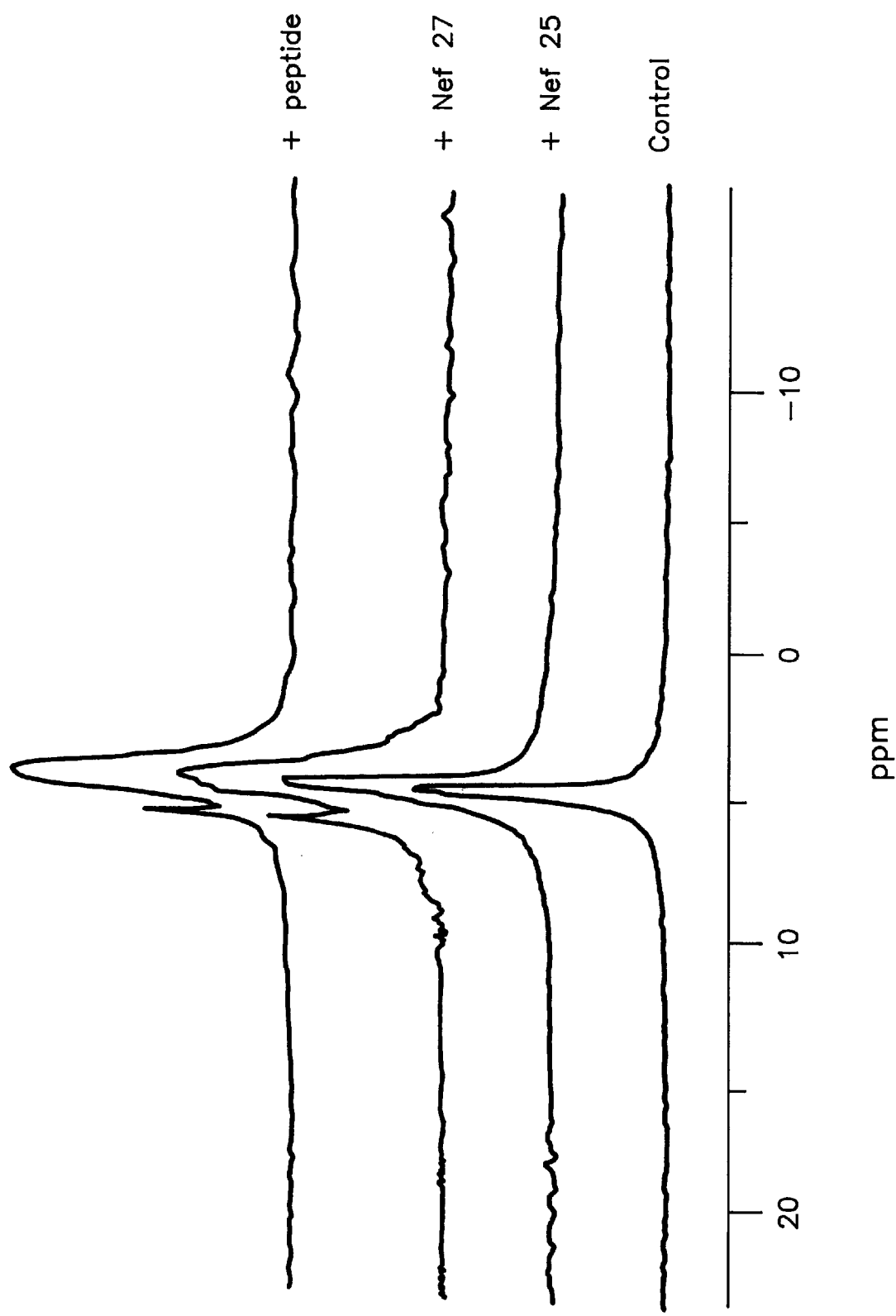
FIG. 6 shows $^{31}P$ NMR spectra of SUV after addition of $Nef_{2-19}$ peptide, Nef 27 and Nef 25.

Nef 27 and Nef peptide both induce isotropic peaks in $^{31}$P NMR spectra of SUV, whereas Nef 25 does not do this. This is illustrated in FIG. 6. The sharp line of the phospholipid vesicles alone is characteristic of a highly-curved lipid bilayer above its transition temperature. This is also seen for Nef 25. The broadening and appearance of an additional peak seen with Nef 27 and the Nef peptide are both characteristic of bilayer disruption, which is a necessary precondition for vesicle fusion.

EXAMPLE 5

Tryptophan UV Fluorescence

Figure 7:
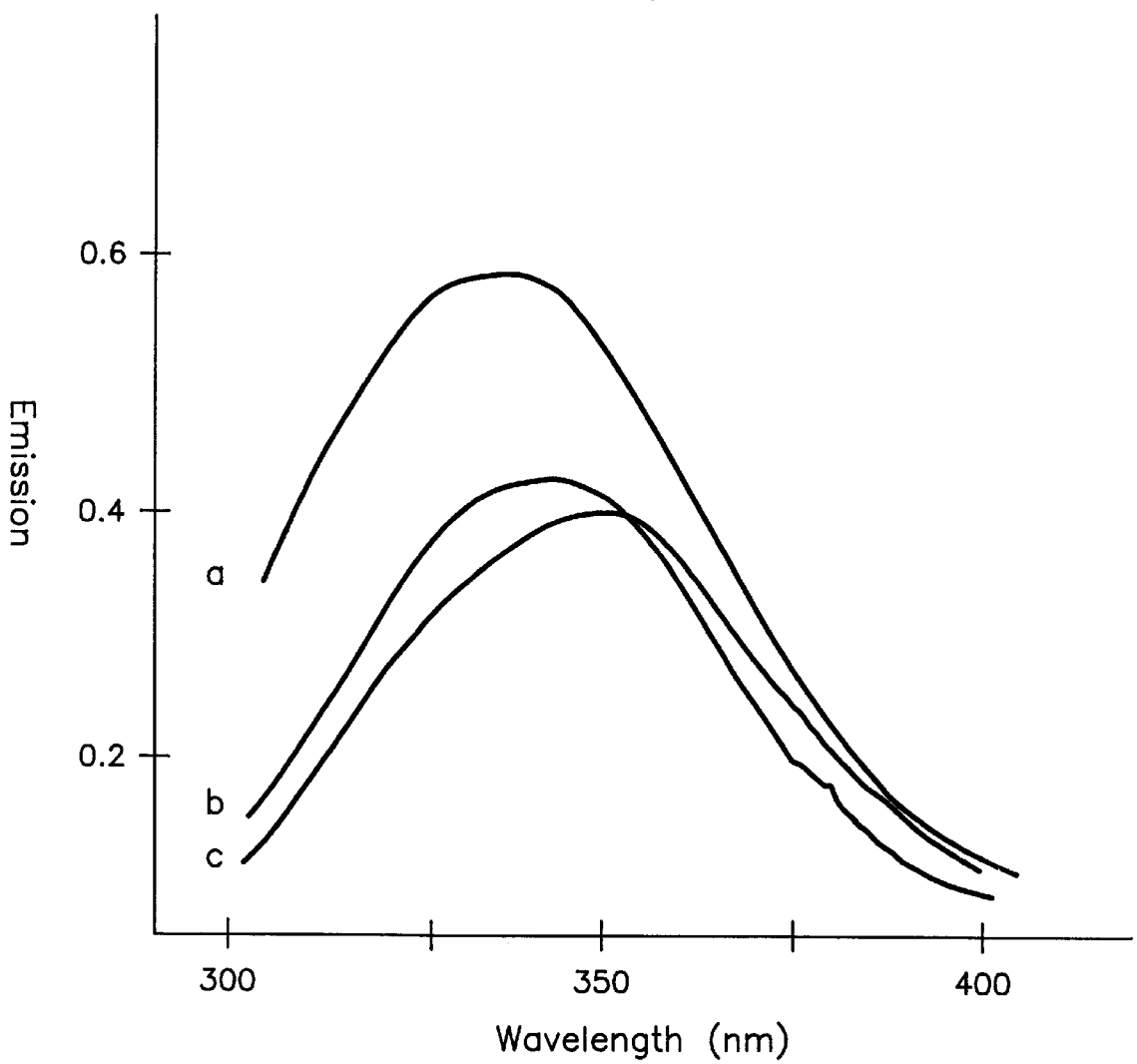
FIG. 7 shows tryptophan fluorescence spectra of $Nef_{2-19}$ peptide in water, ethanol and SUV.

The fluorescence spectra of Nef peptide in buffer and after the addition of 35 mg/ml SUV, giving a peptide/lipid ratio (P/L) of 1/100, is shown in FIG. 7. The blue shift of the tryptophan emission is characteristic of the change in environment from an aqueous to a hydrocarbon medium. The position of the tryptophan in the bilayer was probed by adding the peptide to systems containing various nitroxide spin probes which quench its fluorescence. The results are set out in Table 2.

TABLE 2

Quenching of Nef peptide tryptophan emission by nitroxides in different environments

| P/L | Control | Buffer + TCC | SUV + 5 PC-SL | SUV + 12 PC-SL | SUV + 16 PC-SL |
|---|---|---|---|---|---|
| 1/200 | 1.00 | 0.347 | 0.269 | 0.967 | 0.941 |
| 1/100 | 1.00 | — | 0.286 | 0.835 | 0.908 |
| 1/50 | 1.00 | — | 0.274 | 0.617 | 0.629 |
| 1/25 | 1.00 | — | 0.218 | 0.338 | 0.413 |

It can be seen that TCC, which does not penetrate the bilayer, has no effect on the tryptophan fluorescence in the presence of SUV, although it does quench the fluorescence of the peptide in buffer. At peptide/lipid ratios<1/100 the tryptophan is quenched mainly by the 5PC-SL, while at a peptide/lipid>1/50 there is quenching also by the 12 and 16 PC-SL.

Figure 8:
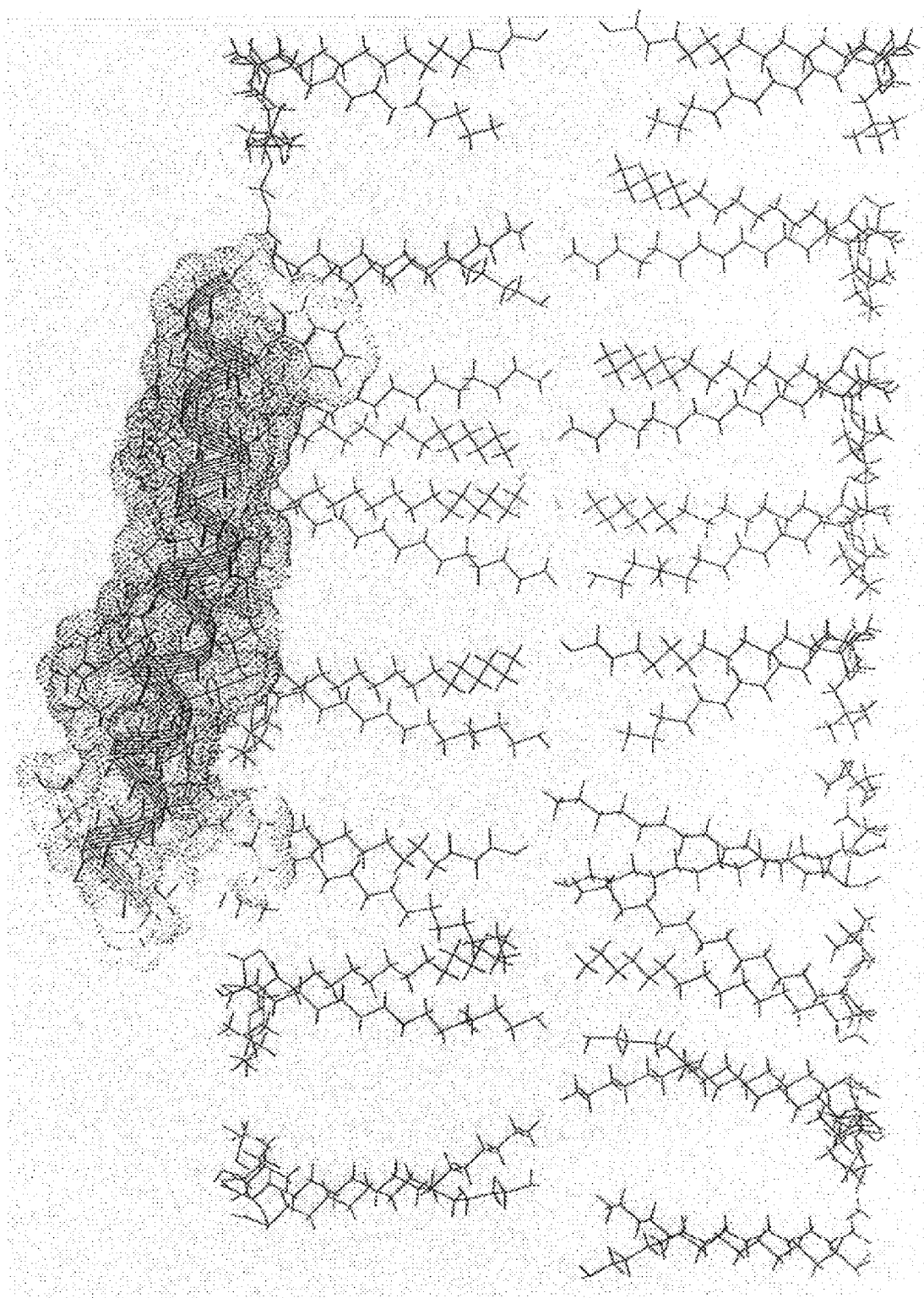
FIG. 8 depicts a molecular model showing monomeric Nef peptide with its hydrophobic region inserted in the hydrophobic region of a lipid binary, and its polar residues oriented to the external aqueous medium.

The Nef peptide appears to interact with bilayer lipid membranes in a number of ways. The blue shift in the fluorescence emission of tryptophan which occurs after addition of SUV shows that these residues are buried in the hydrocarbon region of the lipid bilayer. This observation is confirmed by the lack of quenching of the fluorescence by the water-soluble TCC when SUV are present in the system. Since this effect was present at a P/L of 1/50 and 1/25 it appears that the SUV took up the peptide quantitatively at quite high P/L. On the other hand, at P/L<1/100 the tryptophan fluorescence was quenched by 5 PC-SL, while at P/L>1/50 it was also quenched by 12- and 16 PC-SL. These results suggest that at low P/L the peptide is associated with the surface region of the bilayer, with the tryptophans located in the upper region of the bilayer hydrocarbon, possibly as shown in FIG. 8. In contrast, at high P/L the peptide is located so that at least one of the tryptophans is located in the 12–16 carbon region of the bilayer, possibly assuming a multimeric trans-membrane conformation. The increase in light scattering on addition of the peptide to SUV suggests that it aggregates phospholipid vesicles. Furthermore, the occurrence of a marked isotropic line in the $^{31}$P NMR spectra of SUV after the addition of the Nef peptide to a P/L of 1/100 suggests that the association of the peptide with the bilayer leads to the formation of non-lamellar lipid phases, an event which precedes membrane fusion. The Nef 27 protein also increases light-scattering rapidly when added to SUV, and causes the appearance of an isotropic line in the $^{31}$P NMR spectra of the SUV.

Because Nef 25 causes none of these effects, it appears that the N-terminal region of Nef 27 contains a membrane-active domain. While fusion events inside normal cells occur physiologically, unscheduled fusion brought about by the presence of a foreign membrane-active molecule such as Nef may be very disruptive as a result of breakdown of intracellular compartmentation. For example, the membrane-fusing properties of Nef may be relevant to its actions in downregulation of CD4 by hindering transport of the antigen to the cell surface. The N-terminal stretch of the protein may, therefore, be a useful therapeutic target.

EXAMPLE 6

Effect of Nef 27 On Syncytium Formation In HIV-1-Infected Cells

Different allelic forms of the Nef protein are produced in the course of HIV-1 virus infection, depending on the isolate of the virus being studied. In our laboratory we have two such isolates, one of which produces marked syncytium formation and cytopathic effect and is designated syncytium-inducing (SI), and a second which does not induce syncytium, and which causes a lesser degree of cell death. This latter isolate is designated non-syncytium inducing (NSI). Charaterisation of cells infected with these isolates shows that the SI isolate was able to down-regulate surface CD4 expression, whereas the NSI isolate did not. We have shown that Nef protein of the HIV-1 strain designated pNL4.3 is able to down-regulate the surface CD4 expression. A series of monoclonal antibodies was able to recognise different allelic forms of expressed Nef protein, thus demonstrating structural differences between these allelic forms. The course of infection induced by the NSI strain was altered by addition of recombinant Nef 27 of the pNL4.3 allelic form. This indicates that the recombinant Nef 27 is able to restore the ability of the virus to form syncytia, thereby allowing increased clumping of the cells. In contrast to the effect of Nef 27, the N-terminal truncated Nef 25 protein was not able to induce this restoration of function.

EXAMPLE 7

Reactivity of Anti-Nef$_{(15-27)}$ With Recombinant Nef 27 and Nef 25 In Immunoblotting The reactivity of sheep anti-Nef$_{(15-27)}$ with recombinant Nef 27 and Nef 25 protein was determined by immunoblotting. Antibodies to the immunogenic peptide (AVRERMRRAEPAA) were purified by affinity chromatography. The antibody preparation used in the immunoblotting experiments was essentially free of antibodies to the immunogenic carrier protein and coupling agent. Purified recombinant Nef 27 and Nef 25 (0.12–1.0 μM) were electrophoresed in a SDS-13% polyacrylamide gel (SDS-PAGE) and subsequently transferred to Hybond-C nitrocellulose (Amersham, Buckinghamshire, England) for 1 h at 100 V using a Bio-Rad protein transfer cell (Bio-Rad, Richmond, Calif.). Membranes were pre-incubated with 1% bovine serum albumin (BSA) for 2 h at room temperature and then reacted with affinity-purified sheep anti-Nef$_{(15-27)}$, diluted 1:100, overnight at 4° C. After three washes in PBS/0.05% Tween 20, the blots were incubated with donkey anti-sheep immunoglobulin conjugated to biotin, diluted 1:500, for 1 h at room temperature. After extensive washing as described above the membranes were incubated with streptavidin-conjugated horse radish peroxidase, diluted 1:500, (Amersham) for 1 h at room temperature. All dilutions were made with 1% BSA in PBS. After further washing the membrane was developed with phenylenediamine substrate (Dako, Dakopatts, Denmark).

Results of immunoblotting reactions in which E.coli-derived Nef 27 and Nef 25 were reacted with anti-Nef$_{(15-27)}$ are shown in FIGS. 9A and 9B. Strongly reactive bands of approximately 27 kDa and 25 kDa were observed with Nef 27 and Nef 25 respectively. The antibodies could detect at least 0.15 μmol of either Nef 27 or Nef 25 by immunoblotting, indicating equivalent recognition of both proteins by this polyclonal antibody.

EXAMPLE 8

Detection Of HIV-1 Nef Protein In HIV-1 Infected MT-2 Cells

MT-2 cells ($3 \times 10^7$ cells) grown to confluence were harvested from culture, placed in a 50 ml polypropylene test tube (Nunc, Roskilde, Denmark) and adsorbed with HIV-1 (isolate 228200; 27) for 2 h at 37° C. with agitation. After this incubation period the cells were resuspended in supplemented RPMI 1640 medium and incubated at 37° C. for 4 days. MT-2 cells incubated in medium alone were included as a control. Following the 4 day incubation period, HIV-1 infected MT-2 cells and control cells were harvested from culture, resuspended in lysis buffer (0.5% Nonidet P40, 0.5% sodium deoxycholate, 50 mm NaCl, 25 mM Tris/HCl. 5 mm Benzamidine/HCl, 10 mm EDTA, 0.1 M Phenylmethyl sulfonyl fluoride in n-propanol and 0.01% sodium azide, pH 8) and the cell lysates electrophoresed, transferred to Hybond-C nitrocellulose paper (Amersham) and immunoblotted with anti-Nef$_{(15-27)}$ as described above. Nef protein was detected in amounts similar to those seen on electroporation of cells with recombinant protein.

EXAMPLE 9

Electroporation of E. coli-Derived HIV-1 Nef 25 or 27 Into T-Cell Lines and PHA-Activated PBMC An efficient electroporation technique termed Baekonization was used to transfer BSA, recombinant Nef 27 or recombinant Nef 25 protein into PBMC and the CD4$^+$ T-cell lines MT-2, CEM and Jurkat cells. This form of electroporation uses electric field rather than electric charge to transfer macromolecules across the cell membrane and results in greater cell viability. The Baekon 2000 Advance Macromolecule Transfer System (Baekon, Inc. Fremont, Calif.) was chosen because of its ease of operation and its electrode configuration, which allows rapid macromolecule transfer. Optimal conditions for electroporation were standardised using CEM cells at a concentration of $5 \times 10^5$ cells/100 μl, 1 μM or recombinant HIV-1 Nef 27 or Nef 25 and electroporation medium (1.5 mM Na$_2$HPO$_4$, 0.5 mM KH$_2$PO$_4$ and 0.27 M sucrose, pH 7.0).(26). PBMC or T-cells harvested from culture during the middle of their exponential growth phase were washed once with PBS and resuspended in electroporation buffer at a concentration of $5 \times 10^6$ cells/ml. Cells were then mixed with 0.5–6.0 μM of Nef 27 or Nef 25 in a final volume of 80 μl containing $8 \times 10^5$ cells and incubated for 10 min on ice. Cells were then electroporated, washed twice with ice-cold PBS, and incubated with supplemented RPMI1640 medium. Control cells included those that were electroporated without any Nef 27, Nef 25 or BSA, and cells that were electroporated with BSA at an equivalent protein concentration. After testing various parameters, the settings which gave optimal electroporation with the Baekon apparatus were chosen as follows: amplitude, 5 kV; pulse frequency, $2^8$; burst time, 0.8; cycle number, 10; pulse width 160μ and distance of electrode from surface of buffer, 1.32 mm. Immediately after electroporation PBMC were stimulated with PHA as described above.

FIG. 10 shows a Nef-specific 27 kDa or 25 kDa band detected in CEM cells electroporated with Nef 27 or Nef 25, respectively. The band intensities obtained after reaction of anti-Nef$_{(15-27)}$ with recombinant protein (0.75–1.0 μmol) were similar to those obtained after reaction of the antibodies with lysates prepared from cells electroporated with the recombinant protein. This indicates that most of the protein placed in contact with the cells during electroporation was taken up by the cells. Similarly, the level of Nef protein incorporated into cells after electroporation corresponded to the amount detected in MT-2 cells 48 h post-infection with HIV-1, isolate 228200 (data not shown). This indicates that the molar concentration of Nef produced in naturally infected cells is similar to that in electroporated cells.

EXAMPLE 10

Detection Of Electroporated HIV-1 Nef 25 Or 27 By Indirect Immunofluorescence

Immediately after electroporation, cells were washed twice with PBS and prepared for detection of HIV-1 Nef by indirect immunofluorescence staining. For detection by immunofluorescence a drop of cell suspension was air dried onto glass slides and fixed with freshly prepared 3.5% paraformaldehyde for 10 min at room temperature. The fixed cells were washed in PBS and either rendered permeable by treatment with 0.05% Nonidet P40 (BDH Chemicals Ltd, Poole, Dorset) in PBS for 5 min at room temperature, or incubated for 5 min in PBS alone. The cells were incubated with 1% BSA/PBS for 30 min at room temperature in a humidified chamber prior to staining to reduce non-specific binding. The cells were then incubated with sheep anti-Nef$_{(15-27)}$ (diluted 1:100), pre-immune sheep serum (diluted to the same protein concentration as the specific antibodies), mAb NF2B2, mAb AC6, mAb AG11, anti-Nef mAb (NEN) or anti-Nef mAb (ABT) or mouse monoclonal isotype control in a humidified chamber overnight at 4° C. Following extensive washing with PBS, the slides were incubated for 30 min at room temperature in a humidified chamber with fluorescein isothiocyante (FITC)-conjugated donkey anti-sheep IgG (diluted 1:50; Amersham) or FITC conjugated sheep anti-mouse IgG (diluted 1:50; Amersham). All dilutions were carried out in PBS containing 1% BSA. Specimens were examined by fluorescence microscopy using a narrow band blue filter of 488 nm.

Examination of MT-2 cells and PBMC electroporated with Nef 27 by indirect immunofluorescence using anti-Nef$_{(15-27)}$ showed that after electroporation virtually the entire population of cells contained Nef 27. Similarly, 100% of MT-2 cells and PBMC electroporated with Nef 25 showed intense fluorescence when reacted with anti-Nef$_{(15-27)}$ indicating that after electroporation 100% of cells contained Nef 25. Similar results were obtained with CEM and Jurkat cells. Staining of both permeabilised and non-permeabilised cells using several antibodies specific for Nef was performed, and the results confirmed that the protein was inside the cell rather than located on the cell surface. Reaction of mock-electroporated cells with anti-Nef$_{(15–27)}$ produced only very low fluorescence, considered to be background staining, thus confirming the specificity of the antibodies for HIV-1 Nef protein. The pattern of flurorescence observed after reaction of anti-Nef$_{(15–27)}$ with Nef 27- or Nef 25-containing cells showed both proteins to be predominantly located at the plasma membrane, and to a much lesser extent elsewhere in the cell, in all cell types analysed. The stability of the Nef protein incorporated in CEM cells was examined by taking samples at various times after electroporation. Although both Nef 27 and Nef 25 protein were still present in electroporated cells at 48 h post electroporation, less protein was detected.

Examination of permeabilised PBMC and MT-2 cells electroporated with Nef 27 or Nef 25 using mAbs AG11, AE6 and anti-Nef mAb ABT (all directed against the C-terminus of Nef) showed intense fluorescence staining, located predominantly at the plasma membrane and to a much lesser extent in the cytoplasm in almost 100% of cells electroporated, when these antibodies were reacted with permeabilised cells. This indicates that virtually all cells in these populations incorporated Nef 27 or Nef 25 during electroporation. The same observations were made with the other CD4+ve cell lines tested. Similar fluorescence staining, occurring predominantly at the plasma membrane, was also observed when antibodies directed at the N-terminus of Nef (NF2B2 and anti-Nef$_{(15–27)}$ polyclonal and monoclonal antibodies) were reacted with permeabilised MT-2 cells or PBMC electroporated with Nef 27. Intense membrane-located fluorescence was also observed when anti-Nef$_{(15–27)}$ (polyclonal or monoclonal) was reacted with Nef 25 electroporated MT-2 cells and PBMC; however, no significant fluorescence staining was observed when NF2B2 was reacted with the cells. Only low background fluorescence was observed when either AE6, AG11, ABT, NF2B2 or anti-Nef$_{(15–27)}$ were reacted with mock-electroporated cells indicating the specificity of the staining reactions for Nef.

Reaction of non-permeabilised MT-2 cells or PBMC electroporated with either Nef 27 or Nef 25 with any of the C-terminal monoclonal antibodies gave excellent low background staining, confirming that at least the C-terminal regions of the Nef proteins were inside the treated cells rather than bound to the cell surface. However, reaction of non-permeabilised cells which had been electroporated with Nef 27 or Nef 25 with antibodies directed at the N-terminus (anti-Nef$_{(15–27)}$, both polyclonal and monoclonal antibodies) of Nef showed intense membrane-located fluorescence, indicating exposure at the cell surface of the N-terminal region of the Nef protein. No detectable fluorescence was observed when non-permeabilised, mock-electroporated cells were reacted with antibodies directed against the C-terminus of Nef. As a control for ability of antibodies to traverse cell membranes prior to permeabilisation, antibodies specific for mitochondrial proteins were included in the staining procedures. Fluorescence staining specific for mitochondrial proteins was only observed when MT-2 cells were permeabilised with NP40 treatment. Only low background fluorescence staining was observed when the mitochondrial-protein antibody was reacted with non-permeabilised cells (Data not shown). Thus for the procedure used in this study, permeabilisation treatment is required for antibodies to traverse the plasma membrane, whilst fixation with paraformaldehyde as performed in this study, does not lead to cell membrane fenestration.

EXAMPLE 11

Trypsin Cleavage of Cell Surface-Located Nef Protein

MT-2 cells ($5\times10^6$/sample) electroporated with Nef 27, Nef 25 or mock-electroporated as described above were resuspended in a 1 ml solution of trypsin/versene for two minutes at 37° C. After this incubation period the cells were extensively washed three times in 50 ml of PBS. After washing, the cells were resuspended at a concentration of $5\times10^6$ cells/ml in PBS and a drop air-dried onto glass slides and fixed as described above. After fixation the cells were extensively washed in PBS, and either permeabilised by treatment with 0.05% (v/v) NP40 as described above or incubated in PBS for the same period of time. After incubation in 1% (w/v) BSA/:BS as described above, the cells were incubated with sheep anti-Nef$_{(15–27)}$ or a mAb directed at the C-terminus (each diluted 1:100) overnight at 4° C. The cells were then washed, reacted with FITC-conjugated donkey anti-sheep Ig or FITC-conjugated sheep anti-mouse Ig (both diluted 1:50) and viewed using fluorescence microscopy as described above.

Treatment of non-permeabilised and electroporated cells with trypsin abolished the ability of the N-terminal Nef antibodies to react with electroporated cells. However, reaction of antibodies directed against the C-terminal region of Nef with cells which were permeabilised following trypsin treatment still showed fluorescence staining associated with the membrane.

EXAMPLE 12

Analysis Of Cell Surface Markers On Cells Containing E. Coli-Derived Nef 27 or Nef 25

Flow cytometry was used to examine whether the levels of CD4, CD25, CD2, CD7 and transferrin receptor (TFR) varied as a consequence of the incorporation of Nef 27 or Nef 25 protein into the CD4$^+$-T cells, MT-2, CEM and Jurkat and PBMC. Cells which underwent a mock-electroporation and cells electroporated with BSA were also used for comparison.

For quantitation of cell surface CD4 and IL-2 R, mock electroporated cells or cells containing electroporated recombinant Nef 27, Nef 25 or BSA were incubated n supplemented RPMI 1640 medium in 24 well Costar plates (Nunc) for 48 h at 37° C. Samples of cells were taken every two hours until 10 h post-electroporation, and again at 24 h post-electroporation. Upon harvesting from culture, the cells were washed once with PBS and incubated with either fluorescein isothiocyante-conjugated-anti-CD4 (Leu 3a+ Leu3b), -anti-CD25, -anti-transferrin receptor (TFR), -anti-CD2, or -anti-CD7 antibody (all from Becton Dickinson, San Jose, Calif.) and the appropriate isotype controls, for 1 h on ice. After this incubation period, cells were washed twice in PBS and fixed with 3.5% paraformaldehyde for 10 min at room temperature. Cells were subsequently analysed by flow cytometry using the Facstar Plus (Beckton Dickinson, San Jose, Calif.).

Figure 11A:
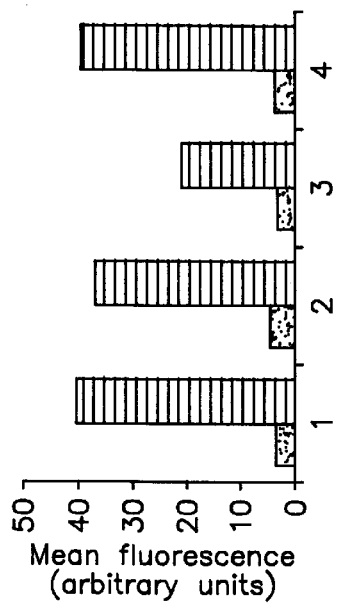
Figure 11B:
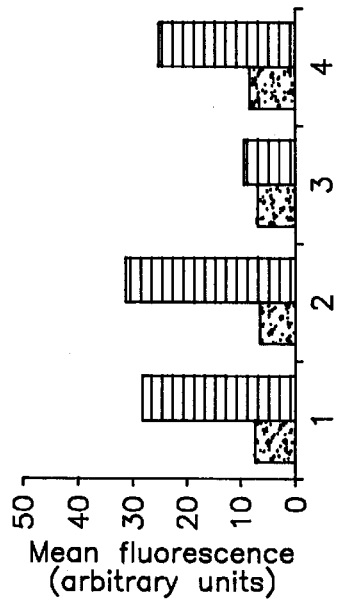
Figure 11C:
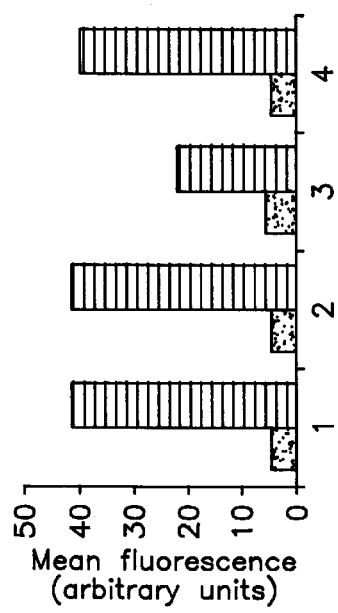
Figure 11D:
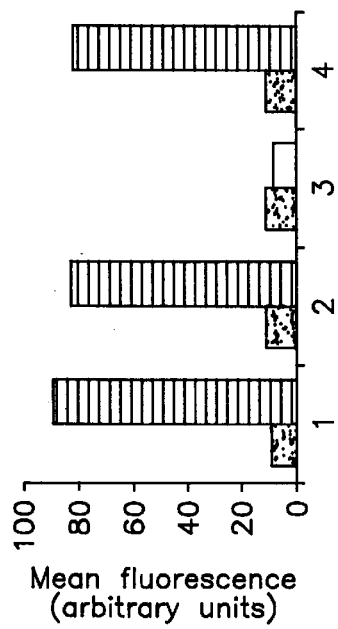

Strong specific fluorescence staining was obtained after reaction of anti-CD4, anti-TFR and anti-CD7 with MT-2, CEM and Jurkat cells which were mock-electroporated or electroporated with BSA. Representative results showing MT-2 cells after reaction with anti-CD4, or the appropriate isotype control, are shown in FIG. 11A. Strong fluorescence staining was also obtained after reaction of PBMC which had been mock-electroporated, or electroporated with BSA, with anti-CD4 or anti-CD2. Results showing PBMC after reaction with anti-CD4 or isotype control monoclonal antibodies are depicted in FIG. 11B. The levels of expression of these surface molecules were comparable with those in control cells which did not undergo electroporation, indicating that the electroporation process did not alter the expression of these cell surface antigens. Similarly, strong surface-located fluorescence was obtained after reaction of MT-2 cells, or PHA-activated PBMC which had been mock-electroporated or electroporated with BSA, with anti-CD25 (FIGS. 11C and 11D).

In contrast to control cells, MT-2, CEM and Jurkat cells and PBMC containing HIV-1 Nef 27 displayed reduced expression of cell surface CD4. The level of surface CD4 in each of the CD4$^+$ cell liens and PBMC was reduced by 30–50% at 24 h post-electroporation (FIGS. 11A and 11B). All cells in the T-cell line populations and all CD4$^+$ cells in the PBMC population showed significantly reduced CD4 surface expression ($p<0.001$, Student's t-test). Thus, all T-cells containing Nef 27 displayed significantly reduced levels of surface CD4. In a typical experiment, flow cytometric analysis of PBMC mock-electroporated or electroporated with BSA and subsequently reacted with anti-CD4 24 h post-electroporation showed 40% of CD4$^+$ T-cells distributed around a mean fluorescence intensity of 42. In contrast, CD4$^+$ PBMC which contained Nef 27 after electroporation showed a single peak of fluorescence with a mean fluorescence intensity of 21 after reaction with anti-CD4. By way of comparison, fluorescence staining obtained after reaction of PBMC electroporated with Nef 27, BSA or mock electroporated with an isotype control was distributed around a mean fluorescence intensity of 7. Levels of CD2, TFR and CD7 on the surface of these cells were not affected by the presence of HIV-1 Nef 27.

Expression of cell surface TFR and IL-2 R in MT-2 cells electroporated with HIV-1 Nef 27, HIV-1 Nef 25, BSA or mock electroporated cells is shown in FIG. 12. MT-2 cells and PHA-activated PBMC containing Nef 27 protein also showed significantly reduced expression of IL-2 R. Since the other T4-cell lines used in this study constitutively express only very low levels of IL-2 R, the effect of HIV-1 Nef 27 on the expression of IL-2 R in these cells was not examined. In the case of MT-2 cells, mock-electroporated or electroporated with BSA, a single peak of fluorescence distributed around a mean of 90 was obtained after reaction of the cells with anti-DC25. In comparison, the peak of fluorescence obtained after reaction of MT-2 cells which contained Nef 27 with anti-CD25, 24 h post-electroporation, was distributed around a mean fluorescence of 10 (FIGS. 11C and 11D). This level of fluorescence staining was similar to that produced after reaction of the isotype control with the cells, indicating that IL-2 R expression was reduced to background levels by the presence of Nef 27. All cells in the MT-2 population demonstrated reduced expression of IL-2 R (FIG. 11C). In the case of PHA-activated PBMC, the percentage of IL-2 R positive cells was reduced from 19% to 4% at 24 h post-electroporation of Nef 27 into these cells (FIG. 11D). Again, the expression of TFR, CD2 and CD7 was not affected by the incorporation of Nef 27 in these cells.

EXAMPLE 13

Nef 25 Does Not Down-Regulate Expression Of CD4 or IL-2 R

Nef 25 was also electroporated into the various T-cell lines and PBMC to investigate its effect on the expression of surface CD4 and IL-2 R. Surprisingly, CEM, MT-2 and Jurkat cells and PBMC electroporated Nef 25 showed normal expression of surface CD4 (FIGS. 11A and 11B). The fluorescence staining obtained after reaction of anti-CD4 with the Nef 25 containing cells was similar in fluorescence intensity to that obtained after reaction of the antibody with control cells (mock-electroporated or BSA electroporated cells) (FIGS. 11A and 11B). Similarly, Nef 25 had no effect on the expression of IL-2 R in MT-2 cells or PHA-stimulated PBMC (FIGS. 11C and 11D). The fluorescence staining after reaction of MT-2 cells or PHA-activated PBMC which contain Nef 25 with anti-CD25 was similar to that obtained with control cells. Thus, HIV-1 Nef 27, but not Nef 25, causes a down-regulation in expression of CD4 and IL-2 R in various T-cell lines and in PBMC.

EXAMPLE 14

Time Course Of CD4 And IL-2 R Down-Regulation By HIV-1 Nef 27

Harvesting of MT-2 cells containing Nef 27, Nef 25 or mock-electroporated MT-2 cells at various times post-electroporation showed that the reduction in expression of surface CD4 and IL-2 R as a result of Nef 27 incorporation into the cells begins to occur 8–10 h after electroporation. Samples of cells containing Nef 27 harvested at 0, 2, 4 and 6 h post-electroporation showed that the levels of surface CD4 and IL-2 R were similar to those expressed in control cells. However, between 8 to 10 h post-electroporation levels of CD4 and IL-2 R were reduced by approximately 10T and 30%, respectively. No further reduction in expression of surface CD4 or IL-2 R was seen 24 h post-electroporation.

EXAMPLE 15

Down-Regulation Of DC4 And IL-2 R By HIV-1 Nef 27 Is Dose-Dependent

To investigate whether the effect of Nef 27 on the expression of surface CD4 and IL-2 R is dependent upon the amount of Nef 27 protein, CEM and MT-2 cells were electroporated with various concentrations of Nef 27 or Nef 25 protein. The effect of these proteins on CD4 and IL-2 R cell surface expression was subsequently measured at 24 h post-electroporation. Electroporation of CEM and MT-2 cells with 0.1–3.0 μmol of Nef 27 showed a dose-dependent effect on the expression of CD4 in the case of CEM cells and of both CD4 and IL-2 R in the case of MT-2 cells. The level of down-regulation of CD4 and IL-2 R was highest when 3.0 μmol of Nef 27 was used for electroporation. This resulted in 50% reduction in surface CD4 in CEM cells, and reduction of IL-2 R to near background levels in MT-2 cells. The negative regulatory effect of HIV-1 Nef 27 upon cell surface CD4 and IL-2 R expression in CEM and MT-2 cells was still observed when 0.1 μmol of Nef 27 protein was used for electroporation. In this case reduction of surface CD4 and IL-2 R expression in CEM and MT-2 cells by approximately 6% (CD4 in CEM cells) and 13% (IL-2 R in MT-2 cells) was observed.

EXAMPLE 16

Binding of Cellular Proteins to Nef In Vitro

MT-2 cells or PHA-activated PBMC ($3\times10^7$ cells/sample) were washed twice in PBS, resuspended in 300 μl of lysis buffer (0.5% v/v Nonidet-P40, 0.5% w/v sodium deoxycholate, 50 mM NaCl, 25 mM Tris/HCl, 10 mM EDTA, 5 mM benzamidine/HCl, 10 mM phenylmethylsulfonyl fluoride in n-propanol and 0.01% w/v sodium azide, pH 8.0) and incubated on ice for 5 min. After this incubation period the cell lysates were centrifuged at 12,000 g for 10 min and the cytoplasmic extract recovered. The cytoplasmic fraction was then pre-cleared by incubation with 50 μl of a 50% slurry of Glutathione Sepharose 4B (Pharmacia, Uppsala, Sweden) in Tris buffered saline, pH 7.5 (TBS) at 4° C. for 10 min. After centrifugation at 12,000 g for 2 min the supernatant was removed, divided into three 1.5 ml conical tubes (Eppendorf, German) and glutathione (GST; 5 μg/sample), GST-Nef 27 or GST-Nef 25 (5 μg/sample) or TBS added. The cell supernatants and added proteins were then incubated together overnight at 4° C. Next day, 50 μl of a 50% slurry of glutathione Sepharose beads was added to each tube and incubated with continuous agitation for 30 min at room temperature. Each suspension was then cooled on ice for 15 min before the Sepharose was pelleted by centrifugation for 2 min at 12,000 g. The Glutathione Sepharose beads were washed three times with 1 ml of ice-cold TBS containing 0.05% (v/v) NP40. Bound proteins were eluted by incubation of the Sepharose beads with 20 μl of 10 mM glutathione for 10 min at room temperature. After centrifugation the supernatant was removed and stored, and the elution step repeated twice. Aliquots (20 μl) of the eluted material were then electrophoresed on a 13% polyacrylamide, gel and either the separated material detected by silver staining or transferred to Hybond C-Super nitrocellulose (Amersham, UK) and immunoblotted with antibodies reactive with $p56^{lck}$ or CD4.

Figure 13A:
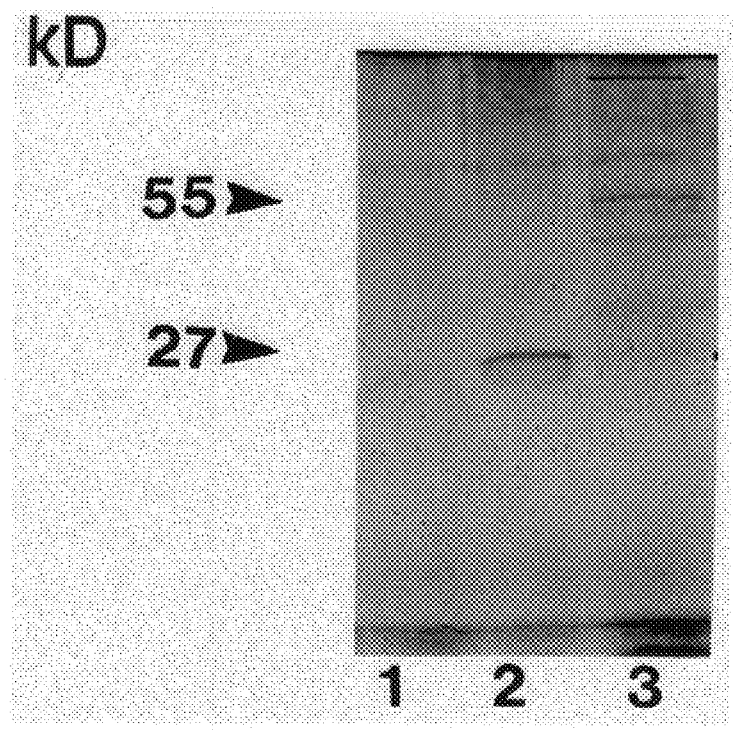
Figure 13B:
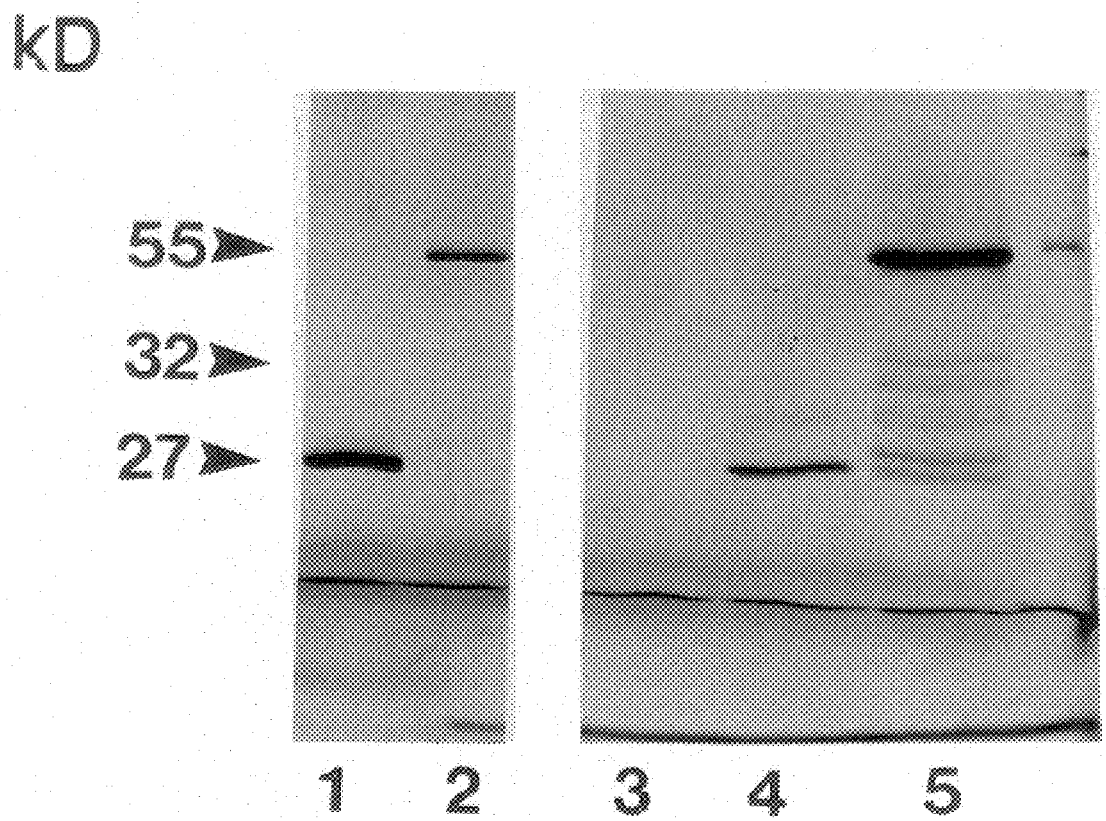
Figure 13C:
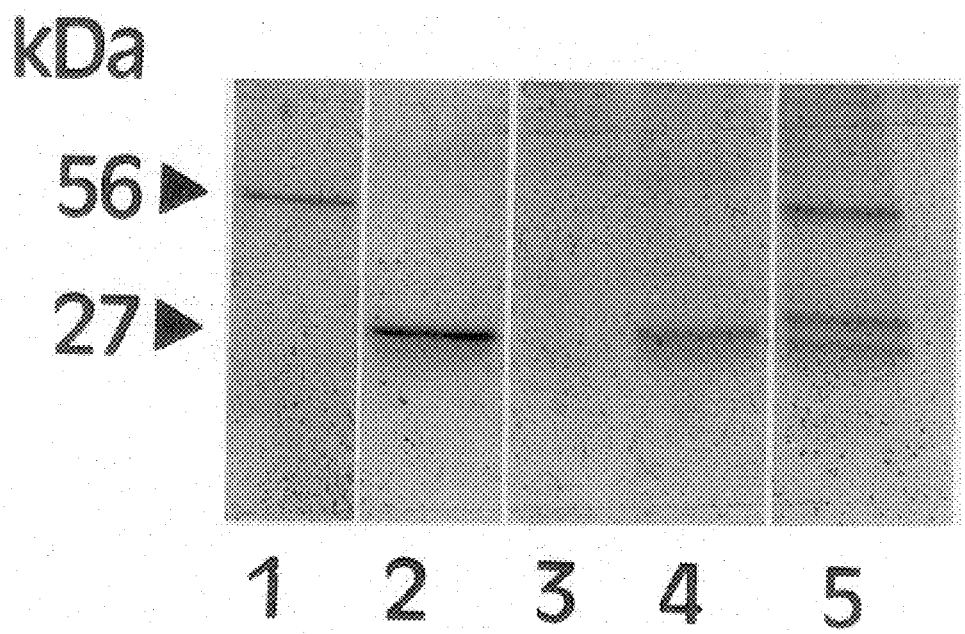

Multiple proteins were precipitated from lysates prepared from MT-2 cells and PHA-activated PBMC when the GST-Nef fusion protein was incubated with the cell lysates. The proteins precipitated from MT-2 cell lysates were approximately 24, 27, 32, 36, 45, 50, 56 and 75 kDa in size whilst proteins prepared from PHA-activated PBMC found to interact with GST-Nef 27 were of 27, 28, 30, 32, 36, 56, 60 and 75 kDa (FIGS. 13a and 13b, respectively). When GST-Nef 25 was used as the binding antigen, proteins of approximately 27, 28 and 56 kDa were precipitated from lysates prepared from PHA-activated PBMC (FIG. 13c). No detectable proteins were precipitated in any case when GST was incubated with the pre-cleared lysates. Similarly, no detectable proteins were precipitated by interaction with the glutathione-Sepharose beads alone, indicating that the proteins precipitated with GST-Nef 27 and GST-Nef 25 formed specific interactions with the Nef proteins. For further confirmation of the specificity of the interaction of these cellular proteins with Nef, recombinant Nef 27 or Nef 25 was added to aliquots of pre-cleared PBMC and MT-2 cell lysates. Addition of exogenous Nef was able to significantly inhibit the binding of each of the proteins to GST-Nef 27 or GST-Nef 25 (Data not shown).

EXAMPLE 17

Identification Of Cellular Proteins Binding To GST-Nef 27 and GST-Nef 25

Figure 14A:
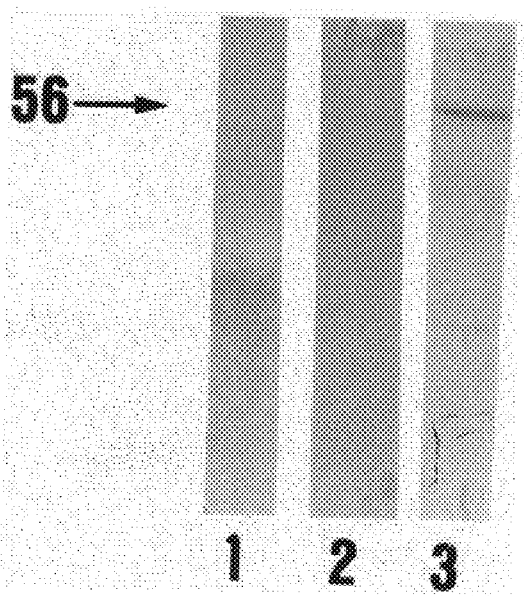
Figure 14B:
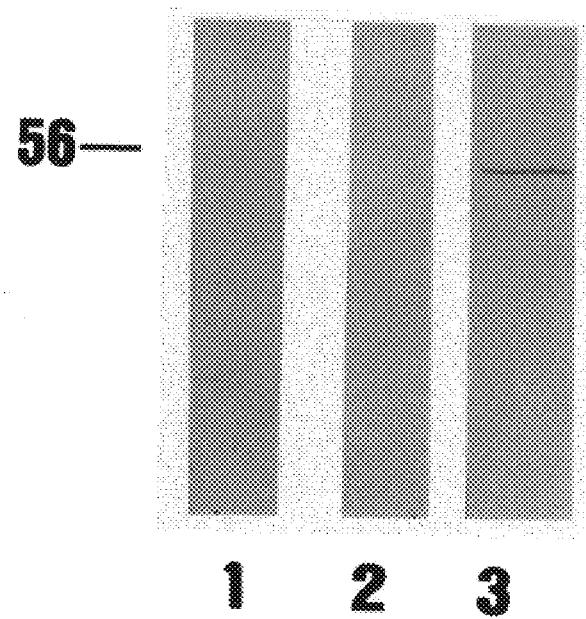

To identify several of the cellular proteins interacting with GST-Nef 27 and GST-Nef 25, the GST-Nef 27 and GST-Nef 25 precipitates prepared from MT-2 cells and PHA-activated PBMC were electrophoresed in a 13% polyacrylamide gel, and subsequently transferred to Hybond-C Super nitrocellulose and probed with anti-$p56^{lck}$ or anti-CD4. Reaction of anti-$p56^{lck}$ with the MT-2 and PHA-activated PBMC cellular proteins precipitated with GST-Nef 27 showed that $p56^{lck}$ was a constituent in the precipitates prepared from the MT-2-cell- and PBMC-GST-Nef 27 precipitates (FIG. 14a and 14b, respectively). $p56^{lck}$ most likely represents the protein identified as 56 kDa. Furthermore, when the PHA-activated PBMC cellular protein precipitate was probed with anti-$p56^{lck}$, the 60 kD phosphorylated isoform of $p56^{lck}$ was also identified to be present (FIG. 14b). The 60 kDa isoform of $p56^{lck}$ was not identified in the cellular proteins precipitated from the MT-2 cell lysate, possibly due to lower amounts of the phosphorylated form present in MT-2 cells as compared with levels present in PBMC (data not shown). The specificity of the reaction with anti-$p56^{lck}$ was verified by using two other antibodies which recognise $p56^{lck}$. Reaction with anti-CD4 of MT-2 and PBMC cellular proteins precipitated with GST-Nef 27 also showed CD4 to be present in precipitates prepared from both MT-2 cells and PBMC (FIG. 15). When cellular proteins precipitated from MT-2 cells or PBMC with GST-Nef 25 were reacted with either anti-$p56^{lck}$ or anti-CD4 in western immunoblotting, neither protein was shown to be present in detectable levels (data not shown).

EXAMPLE 18

T-Cell Activation In Nef-Containing PBMC

Growth factor-dependent DNA synthesis was determined by measurement of [$^3$H]-thymidine incorporation into cellular DNA as previously described (45). Briefly, PHA-activated PBMC ($2\times10^6$/ml) electroporated with Nef 27, Nef 25 or mock-electroporated as described above were incubated in medium for 24 h and then stimulated with IL-2 (Boehringer Mannheim, Germany) at 10, 30 or 100 IU/ml (triplicate samples of $10^6$ cells/sample). After 24 h in culture, cells were pulsed with [$^3$H]-thymidine (5 μCi/ml)

for 16 h, and incorporation of radioactivity into DNA was measured by liquid scintillation counting. Each sample was assayed in duplicate. The values presented are the mean ±S.D. for three experiments.

The IL-2 proliferative response of PHA-activated PBMC which had been mock-electroporated or electroporated with BSA increased in parallel with the concentration of IL-2. The results are shown in FIG. 16. Proliferation was not significantly altered by electroporation, as control cells treated with IL-2 incorporated similar amounts of [$^3$H]-thymidine to PBMC mock-electroporated or electroporated with BSA. In contrast, incorporation of Nef 27 into PHA-activated PBMC prior to stimulation with IL-2 dramatically reduced the proliferative response of these cells to IL-2. Similarly, Nef 25 treated cells also showed a reduced proliferative response to IL-2; however the effect was not as large as that observed with Nef 27.

EXAMPLE 19

Localisation Of Lck In Nef-Treated Jurkat Cells p56$^{lck}$ as been shown to be associated with the cytoplasmic domains of both DC4 and IL-2 receptor through its N-terminus and C-terminus regions, respectively (46,47). The inhibitory effect of Nef 27 on cell proliferation and on phosphorylation of p56$^{lck}$ in response to IL-2 stimulation may be a direct consequence of the interaction of Nef with p56$^{lck}$. to investigate the possible effect of Nef on cellular distribution of lck, indirect immunofluorescence studies using anti-p56$^{lck}$ were performed on Nef 27-, Nef 25-, BSA- and mock-electroporated Jurkat cells immediately after electroporation, and again at 24 h post-electroporation. Jurkat cells were chosen for these localisation studies since these cells express relatively high levels of p56$^{lck}$. Jurkat cells were electroporated with recombinant Nef 27, Nef 25 or mock-electroporated, and incubated in supplemented RPMI 1640 medium for up to 24 h at 37° C. Cells were harvested at 0, 10 and 24 h post-electroporation, washed twice in PBS and a drop of cell suspension (5×10$^6$ cells/ml) air dried onto glass slides, and fixed in 3.5% paraformaldehyde for 10 min at room temperature. After blocking with 1% fetal calf serum the cells were incubated with anti-p56$^{lck}$, diluted 1:100, at 4° C. overnight. As a control, cells were incubated with normal rabbit serum for the same period of time. Next day the slides were washed three times in PBS and incubated with anti-rabbit conjugated TRITC Ig secondary antibody (Silenus, diluted 1:50) for 1 h at room temperature. After washing in PBS, the slides were viewed using conventional fluorescence microscopy. Intense, predominantly membrane-associated fluorescence specific for p56$^{lck}$ was observed in mock-electroporated and BSA-electroporated Jurkat cells when cells were reacted with anti-p56$^{lck}$ immediately after electroporation. Similarly, cells electroporated with Nef 27 or Nef 25 also displayed intense predominantly membrane associated fluorescence when reacted with anti-p56$^{lck}$ immediately after electroporation. When the electroporated cells were analysed 24 h after electroporation, mock and BSA-electroporated cells still displayed intense, membrane located fluorescence. In direct contrast, Jurkat cells electroporated with Nef 27 showed diffuse fluorescence staining which was of lower intensity compared with that of control cells. Nef 25-treated Jurkat cells also displayed reduced membrane associated fluorescence when reacted with anti-p56$^{lck}$; however the effect was not as marked as observed in Nef 27 treated Jurkat cells.

EXAMPLE 20

IL-2 Dependent And PMA-Induced Phosphorylation Of p56$^{lck}$ Is Inhibited In Nef 27 Treated PBMC Addition of IL-2 to T-cells expressing the high affinity IL-2 R complex results in the transmission of a proliferative stimulus. Increasing evidence suggests that tyrosine protein kinases and serine/threonine protein kinases are involved in IL-2 dependent proliferative signals (48). Indeed, p56$^{lck}$ tyrosine kinase activity is rapidly stimulated following IL-2 addition, and undergoes subsequent IL-2 dependent serine/threonine phosphorylation modifications which result in the retardation in mobility of the p56$^{lck}$ protein by polyacrylamide gel electrophoresis (18). Alterations in phosphorylation of p56$^{lck}$ in response to IL-2 were evaluated in PBMC electroporated with Nef 27, Nef 25 or mock-electroporated. Electroporated PBMC or control PBMC were treated with IL-2 for increasing periods of time. Human PBMC were isolated from normal adults by Ficoll-Paque density centrifugation. Cells were cultured in RPMI 1640 medium supplemented with 10% fetal calf serum in the presence of PHA (10 μg/10$^6$ cells) for 3 days. The PHA-activated PBMC were then incubated in supplemented RPMI 1640 medium for 24 h, and electroporated with Nef 27, Nef 25 or mock electroporated, as described above. After incubation in medium for a further 24 h to reduce low level production of IL-2, the cells were harvested, washed three times and then incubated with 1000 IU of recombinant IL-2 (Boehringer Mannheim) for 0, 15 and 30 min. After incubation, cells were lysed and analysed for the presence of phosphorylated forms of p56$^{lck}$ by immunoblotting with anti-p56$^{lck}$. For activation of PBMC by phorbol 12-myristate 13-acetate (PMA), cells were mock electroporated or electroporated with Nef 27, Nef 25, BSA as described above, incubated at 37° C. for 24 h and then stimulated with PMA (20 ng/ml) for 4 h at 37° C., after which time the cells were harvested and prepared for immunoblotting with anti-p56$^{lck}$. The results are presented in FIG. 17. Addition of IL-2 to control PBMC resulted in reduced electrophoretic mobility of a portion of p56$^{lck}$. The slower migrating species of p56$^{lck}$ was found to co-migrate with the altered mobility species of p56$^{lck}$ induced after PMA treatment of PBMC (data not shown). Similarly, addition of IL-2 to mock-electroporated PBMC also caused the conversion of a portion of p56$^{lck}$ to its p60 isoform. However, addition of IL-2 to PBMC electroporated with Nef 27 did not result in reduced electrophoretic mobility of p56$^{lck}$. Even after incubation of the Nef 27 treated cells with IL-2 for 30 min, no detectable shift in electrophoretic mobility of p56$^{lck}$ was observed, indicating that Nef 27 inhibited IL-2 dependent signalling, possibly by inhibition of serine/threonine kinases responsible for phosphorylation of the p56$^{lck}$ gene product, or directly by physical association with p56$^{lck}$ (se FIG. 16). In contrast, Nef 25 had no detectable effect on alteration of p56$^{lck}$ in response to IL-2 treatment, as both isoforms, p56$^{lck}$ and p60$^{lck}$ were detected in Nef 25-containing PBMC after treatment with IL-2 (FIG. 17).

The phorbol ester PMA induces the activation of protein kinase C (pkC) in T-cells. A number of cellular proteins, including p56$^{lck}$, are phosphorylated on serine/threonine residues as a result of pkC activation. Treatment of PBMC with Nef 27 also inhibited the phosphorylation of p56$^{lck}$ in response to PMA treatment, as shown in FIG. 18. No inhibitory effect was observed in PBMC treated with Nef 25. Similarly, electroporation of PBMC with BSA or mock-electroporation of cells had no effect on the phosphorylation of p56$^{lck}$ in response to PMA treatment.

EXAMPLE 21

Expression of c-Myb in Nef Treated MT-2 Cells

The nuclear oncoprotein Myb is believed to be an important regulator of cell growth and differentiation in hematopoietic cells, being required for transition of cells from the $G_0/G_1$ phase of the cell cycle to early S-phase. Furthermore, expression of the CD4 gene requires a Myb transcription factor. The levels of c-Myb protein were investigaged in Nef 27, Nef 25, or mock-electroporated MT-2 cells by western immunoblotting using anti-c-Myb. MT-2 cells, harvested during mid-exponential growth phase, were washed twice in PBS and electroporated with recombinant Nef 27, Nef 25, BAS or mock-electroporated as described above. After electroporation the cells were washed twice in PBS, resuspended at a concentrated of $1 \times 10^6$ cells in supplemented RPMI and incubated for 24 h at 37° C. Following the incubation period the cells were washed in PBS again and then resuspended in lysis buffer at a concentration of $10^8$ cells/ml and incubated on ice for 10 min. The cytoplasmic extract was recovered by centrifugation for 10 min at 12,000 g. Cell lysate corresponding to $2 \times 10^6$ cells was electrophoresed in a 13% polyacrylamide gel, transferred to Hybond C-Super nitrocellulose and immunoblotted with anti-c-myb, diluted 1:1000 (49). Following washing in PBS containing 0.05% (v/v) Tween 20 the filters were incubated with anti-rabbit-biotinylated Ig (Amersham), diluted 1:1000 for 1 h at room temperature. The filters were then incubated with Streptavidin-horse radish peroxidase (diluted 1;1000; Amersham) following further washing, and the signal detected using 1,4-dichloronapthol as substrate. The results are shown in FIG. 19. Levels of c-Myb were not affected by electroporation of cells. However, introduction of Nef 27 and also Nef 25 in MT-2 cells significantly reduced the levels of c-Myb as determined by western immunoblotting.

Human CD4$^{30}$ T-lymphocytes form the primary target for infection by HIV-1 in vivo (16). Cells from HIV-infected patients demonstrate aberrant immune responsiveness which may be relevant to the progression from asymptomatic to AIDS (28). The nef gene is present in most strains of HIV-1, HIV-2 SIV (29).

To test whether the HIV-1 nef gene product effects normal cell functioning, we have introduced recombinant Nef 27 and Nef 25 protein, translated from the first and second initiation codons respectively, into various CD4$^+$ T-cells. Cells containing either Nef 27 or Nef 25 were compared with control cells for the effect of Nef on cell surface molecules involved in antigen recognition, signal transduction and development of normal immune response. For the first time, using immunohistochemical techniques, we have shown that HIV-1 Nef 27, but not Nef 25, causes the specific down-regulation of cell surface CD4 and IL-2 R in various T-cell lines and PBMC in a dose-dependent manner. No effect on other cell surface antigens was detected. The novel approach of transferring highly purified recombinant HIV-1 Nef protein across cell membranes by electric field electroporation in appropriately controlled experiments ensures that the properties measured are attributable only to the Nef protein. The dose-dependent effect of Nef 27 suggests that the amount of Nef 27 may be important for full inhibitory activity. The amounts of Nef protein used in this study correspond to those produced during the course of HIV-1 infection in vitro, while localisation of electroporated recombinant Nef protein predominantly at the plasma membrane is in agreement with studies showing naturally occurring Nef to be localised at the cell membrane during infection.

Our results showing the down-regulation of CD4 surface expression by Nef 27 conclusively confirm earlier reports (20, 21) of the down-regulation of CD4 in cells transfected with Nef expression vectors. Guy et al. (20), observed down-regulation of CD4 in CEM cells expressing the HIV-$1_{BRU}$ Nef protein. Similarly Garcia and Miller (21), reported CD4 down-regulation in T-, B- and macrophagic-T cells transfected with HIV$_{SF2}$ Nef. However, it was essential to substantiate these findings, since Gama Sosa et al. (23), reported the down-regulation of CD4 by transfection of cells with plasmid alone.

Progression of in vivo HIV-1 infection to immunological disease is characterised by the depletion of CD4$^+$T-cell population from the peripheral blood system, and by reduced expression of cellular IL-2 R by PBMC even after stimulation with PHA (28, 30, 31, 32). Correspondingly, our laboratory infection of MT-2 cells with HIV-1 isolate 228200 also results in the reduced expression of surface located CD4 and IL-2 R in these cells. Besides its role as the major receptor for HIV-1, CD4, through binding of antigen in the context of MHC class proteins, is intimately involved in the signal transduction pathway which culminates in the clonal expansion of antigen-reactive T-cells and the efficient recruitment of other haematopoietic cells involved in development of the immune response (33).

The down-regulation by Nef protein of surface CD4 and IL-2 R in T-cell lines, but most importantly in PBMC, may be particularly relevant to the progression of HIV-1 infection to disease. The formation of high affinity IL-2 Rs is a well-documented response following stimulation through T-cell receptor (34). Antigent presentation to the T-cell receptor triggers intracellular signalling that subsequently leads to the transcriptional activation of various genes including IL-2. Binding of IL-2 to the high affinity IL-2 R is necessary for cell division and clonal expansion of antigen reactive cells (34, 35). Reduced expression of IL-2 R by HIV-1 Nef 27 may be linked to the inhibition by Nef of IL-2 gene expression through disturbance of the IL-2/IL-2 R autocrine pathway. Alternatively, reduced IL-2 R expression in T-cells may be a result of reduced levels of NFkB protein-binding activity. Regulation of IL-2 R gene expression by the HTLV-1 tax gene product has been reported, in which activation of IL-2 R-alpha gene expression by Tax protein occurs through an interaction with, or activation of, a host transcription factor with properties similar if not identical to NFkB (36, 37). In addition, reduced NFkB protein binding capabilities have been observed in cells transfected with nef (14). The down-regulation in expression of cell surface CD4 and IL-2 R by Nef may represent mutually exclusive events.

Alternatively, the present study may implicate Nef 27 in the modulation of expression or activation of the src protein tyrosine kinase $p56^{lck}$. CD4 is known to be intimately associated with $p56^{lck}$ (19). Phorbol ester-induced modulation of human CD4 is accompanied by the dissociation of $p56^{lck}$ from the receptor, whilst accumulating evidence suggests that $p56^{lck}$ is involved in signal transduction following the interaction of IL-2 with the IL-2 R (18, 38). Expression of Nef during HIV-1 infection may modulate intracellular signals via $p56^{lck}$. Perturbation of this signal transduction pathway may be advantageous for the survival and spread of virus both in vitro and in vivo, resulting in the demise of the T-cell population.

Our results have also highlighted fundamental differences in activity between HIV-1 Nef 27 and Nef 25. Whereas Nef 27 causes the specific down-regulation of both CD4 and IL-2 R, Nef 25 does not affect the cell surface expression of either of these surface antigens. Immunofluorescence detection of electroporated Nef 27 and Nef 25 showed localisation to be predominantly at the plasma membrane for both proteins. This indicates that differences in activity are not a consequence of variation in localisation of the two Nef species. However, the differences in biological activity observed for Nef 27 and Nef 25 suggest that the functional domain of Nef resides at the N-terminus of the protein. Alternatively, deletion of the first 19 amino acids may alter the conformation of the protein such that normal activity is abolished. In either case, this 19 amino acid sequence appears to be essential for the biological function of Nef.

It is previously been shown that during HIV-1 infection there is variation in the level of expression of two species of Nef of approximate Mr 27 and 25 (13,40), but it is not known whether the smaller species results from internal initiation, premature termination or proteolytic cleavage. If Nef 25 arises in vivo by proteolytic cleavage at the C-terminus of Nef 27, or deletion of the 3' end of the nef gene, then it would be a different molecule from the Nef 25 described in this paper. In any case it is possible that there is a selection for a sub-population of viruses that produce high levels of Nef 25, because this protein acts as an inhibitor of a viral protein that interferes with cell propagation. Precedents for viruses encoding antagonistic regulatory proteins exist. Both the bovine papilloma virus E2 open reading frame and the adenovirus EIA region encode two antagonistic regulatory proteins (41, 42). In each case the antagonistic proteins share carboxyl terminal sequences. Hence it is plausible that Nef 25 may be a natural competitor of Nef 27, regulating the negative effect of this protein. This idea is currently being pursued.

Our results demonstrate unequivocally that Nef 27, but not Nef 25, causes reduced expression of cell surface located CD4 and IL-2 R in various CD4+ T-cell lines and in PHA-activated PBMC. We have also demonstrated that HIV-1 Nef 27, and to a lesser extent HIV-1 Nef 25, inhibits the proliferative response of PBMC to IL-2 and the mitogen PHA. Treatment of PBMC with Nef resulted in the inhibition of IL-2 dependent and PMA activation/phosphorylation of the src family kinase $p56^{lck}$. Membrane localisation of $p56^{lck}$ in Jurkat cells was disrupted by treatment with Nef 27 and to a laser extent by treatment with Nef 25, whilst electroporation of Nef 27 and Nef 25 into the HTLC-1 transformed cell line MT-2 dramatically reduced the expression of the protooncogene c-Myb. Precipitation studies using GST-Nef 27 as the binding antigen showed Nef to interact specifically with a number of cellular proteins, two of which have been indentified as $p56/p60^{lck}$ and CD4. The localisation of Nef in both electroporated cells and HIV-1 infected MT-2 cells shows Nef to be intimately associated with the plasma membrane, such that a portion of the N-terminus of Nef is exposed to the extracellular matrix. The orientation of Nef, together with its interaction with numerous proteins of which several are important for antigen recognition and cellular signalling, suggests that Nef plays an intricate role in disturbing normal cellular activation/proliferation pathways.

The difference in activity between Nef 27 and Nef 25 may indicate that the functional domain of Nef resides at the N-terminus of the protein. Alternatively, deletion of the first 19 amino acid residues may affect overall conformation of the protein such that detectable biological activity (defined as the biological activities described herein) is affected. Further investigation of Nef activity in this study shows that while Nef 25 possesses similar activity to Nef 27, the effect of Nef 25 is not as significant as that observed for Nef 27. Hence the first 20 amino acid residues of the Nef protein are required for full activity, as defined in our experiments. A recent report (50) showed that the first 35 amino acid residues of nef are required for transactivation of the HIV-1 LTR, supporting the concept that the N-terminus of Nef is essential for full biological activity.

We have used an *E. coli* expressed GST-Nef 27 and GST-Nef 25 fusion protein as affinity reagents to identify cellular proteins that specifically interact with Nef. A number of proteins from cytoplasmic extracts prepared form PBMC (PHA-activated) and MT-2 cells were identified to interact specifically with Nef. The proteins precipitated from MT-2 cells when GST-Nef 27 was used as the affinity reagent were of 24, 27, 32, 36, 45, 50, 56 and 75 kDa. Corresponding proteins were also identified in the lysates of PBMC, however the 24 kDa species was absent, whilst 28 and 60 kDa species were present in detectable levels in the PBMC preparation only. Two proteins were identified from the lysates as being $p56/60^{lck}$ and CD4. The precipitation of a number of proteins with GST-Nef indicates and indirect interaction for some of these proteins. It is not known whether the interaction of Nef with CD4 and lck is a result of Nef binding directly to either of these proteins or is a result of interaction with other unidentified proteins. A recent study using a baculovirus-expressed nefGST fusion protein as affinity reagent identified a number of proteins from cytoplasmic extracts of Jurkat cells (27). Several of these proteins, p280, p32 and p28, bound only to a myristoylated form of Nef. In our study p32 and p28 proteins were also identified, but bound to a non-myristoylated form of Nef.

Precipitation of $p56^{lck}$ and CD4 with GST-Nef 27 suggests that Nef may disturb signalling pathways by binding directly or indirectly with these proteins. Indeed, Nef may disrupt normal localisation of these proteins resulting in disturbance of cell activation. We have shown that membrane localisation of lck is disrupted following treatment of Jurkat cells with Nef 27, and to a lesser extent following treatment with Nef 25. Fluorescenece staining for lck in Nef 27/Nef 25 treated cells was more diffuse in nature, suggesting movement of the protein away from the membrane. It has been extensively shown that cross-linking CD4 or CD8 with the TCR/CD3 complex markedly enhances stimulation of T-cells compared to cross-linking of the TCR/CD3 complex alone (51). $p56^{lck}$ association with CD4 is critical for the co-localisation of CD4 with the TCR/CD3 complex after T-cell stimulation, whilst the $p56^{lck}$-dependent loss of association between CD4 and the TCR/CD3 complex results in diminished CD4-dependent antigen responsiveness. Thus $p56^{lck}$ appears to play multiple roles in T-cell stimulation (52), and disturbance of $p56^{lck}$ membrane association and or binding of Nef to lck, either directly or indirectly, may greatly impair T-cell responsiveness.

IL-2 has a pivotal role in regulating the proliferation and differentiation of haematopoietic cells. IL-2 exerts its biological effects through binding of specific receptors on the cell surface. Treatment of PBMC with Nef 27 inhibited their proliferative response to IL-2 as judged by [$^3$H]Thymidine incorporation. Treatment of PBMC with Nef 25 also reduced their capacity to respond to IL-2; however, the negative effect of Nef 25 was not as great as that observed with Nef 27. Induction of T-lymphocyte proliferation is dependent on a multiplicity of events, including the activation of numerous genes including the protooncogene c-myb. Several studies provide evidence that c-myb gene function is required for T-lymphocyte proliferation, and is specifically required for transition through $G_1$ or early S-phase of the cell cycle. We have found that Nef affects the levels of c-myb in MT-2 cells, and may be responsible in part for decreased proliferation in response to IL-2. Furthermore, a transcription factor from the Myb family plays a critical role in CD4 promoter function, and therefore contributes to expression of the CD4 gene (50). Thus decreased cell surface expression of CD4 in PHA-activated PBMC and various CD4$^+$ T-cell lines may be a consequence of reduced levels of c-myb. We have shown that Nef 27 inhibits phosphorylation and thus (presumably) activation of $p56^{lck}$ in response to IL-2 or PHA stimulation. This may be a direct result of interaction of Nef with lck, or may indicate inhibition of serine/threonine kinases such as protein kinase C. PMA is a potent activator of protein kinase C. Treatment of PBMC with Nef 27 also inhibited PMA-induced phosphorylation of $p56^{lck}$. Nef 25 did not appear to affect phosphorylation of $p56^{lck}$, but may reflect the more qualitative nature of western block assessment.

Our immunofluorescence studies of Nef localisation in electroporated cells and HIV-1 infected MT-2 cells have shown that the protein is intimately associated with the plasma membrane, whilst a portion of the N-terminus of Nef is exposed to the extracellular matrix. Comparison of permeabilised and nonpermeabilised cells showed that antibodies directed against the C-terminus of Nef detected Nef only in permeabilised cells, whilst antibodies directed against the N-terminal region of Nef reacted with both permeabilised and nonpermeabilised cells containing Nef. HIV-1Bru Nef has been reported to contain a two-peptide domain sequence which as striking similarity to the structure of neuroactive scorpion peptides (53). Nef was also shown to reversibly increase the total K$^+$ current after membrane depolarisation in patch clamp experiments. Such an effect on K$^+$ channels of neuronal cells requires the extracellular presence of Nef. This may be achieved by exposure of part of the molecule to the cell surface.

Further characterisation of the biological activity of Nef and investigation into the mechanism of action is currently being pursued, and will provide useful information for the rational design of antiviral agents able to abrogate the function of Nef. The partial homology between the Nef N-terminal sequence and melittin suggests that the latter is a suitable candidate molecule.

In particular, we are determining the minimum sequence within Nef$_{2-19}$ which can effect the biological function of Nef 27 in the biophysical systems and antigen expression systems disclosed herein. Peptide analogues of $Nef_{2-19}$ are being synthesised. In addition, anti-sense peptides and anti-sense oligonucleotides as well as antibodies and their fragments are being investigated.

A variety of means for introducing analogues or antagonists of $Nef_{2-19}$ peptide into cells are contemplated. Following such introduction, the cells may be challenged with HIV, and parameters such as syncytium formation, down-regulation of CD4, and down-regulation of IL-2 R investigated. Such means include, but are not limited to, lipofection with liposomes, peptide-fat conjugation, electroporation, and transfection of cells with genes expressing anti-sense oligonucleotides directed against the N-terminus of the nef gene, which encodes the $Nef_{2-19}$ peptide.

it will be apparent to the person skilled in the art that while the invention has been described in some detail for the purposes of clarity and understanding, various modifications and alterations to the embodiments and methods described herein may be made without departing from the scope of the invention concept disclosed in this specification.

References cited herein are listed on the following pages, and are incorporated herein by this reference.

REFERENCES

1. Cullen, B.R. "Trans-activation of human immunodeficiency virus occurs via a bimodal mechanism" Cell, 1986 46 973–982.

2. Terwilliger, E.F., Sodroski, J.G., Rosen, C.A., and Haseltine, W.A. "Effects of mutations within the 3' orf open reading frame region down-regulates virus replication" J. Virol., 1986 60 754–760.

3. Arya, S.K., Beaver, B., Jagodzinski, L., Ensoli, B., Kanki, P.J., Albert, J., Fenyo, E.M., Biberfeld, G., Zagury, J.F., Laure, F., Essex, M., Norrby, E., Wong-Staal, F., and Gallo, R.C. "New human and simian HIV-related retroviruses possess functional transactivator (tat) gene" Nature, 1987 328 548–550.

4. Hauber, J., Perkins, A., Heimer, E.P., and Cullen, B.R. "Trans-activation of human immunodeficiency virus gene expression is mediated by nuclear events" Proc. Natl. Acad. Sci. USA., 1987 84 6364–6368.

5. Feinberg, M.B., Jarrett, R.F., Aldolvini, A., Gallo, R.C., and Wong-Staal, F. "HTLV-III expression and production involve complex regulation at the levels of splicing and translation of viral RNA" Cell, 1986 46 807–817.

6. Guy, G., Kieny, M.P., Riviere, Y., Le Peuch, C., Dott, K., Girard, M., Montagnier, L., and Lecoco, J.P. "HIV F/3' orf encodes a phosphorylated GTP-binding protein resembling an oncogene product" Nature, 1987 330 266–269.

7. Klotman, M.E., Kim, S., Buchbender, A., De Rossi, A., Baltimore, D., and Wong-Staal, F. "Kinetics of expression of multiply spliced RNA in early human immunodeficiency virus type 1 infection of lymphocytes and monocytes" Proc. Natl. Acad. Sci. USA, 1991 88 5011–5015.

8. Ratner, L., Haseltine, W., Patarca, R., Livak, K.J., Starcich, B., Josephs, S.F., Doran, E.R., Rafalski, J.A., Whitehorn, E.A., Baumeister, K., Ivanoff, L., Petteway, S.R. Jr., Pearson, M.L., Lautenberger, J.A., Papas, T.S., Ghrayeb, J., Chang, N.T., Gallo, R.C., and Wong-Staal, F. "Complete nucleotide sequence of the AIDS virus, HTLV-III" Nature, 1985 313 277–284.

9. Wain-Hobson, S., Sonigo, P., Danos, O., Cole, S. and Alizon, M. "Necleotide sequence of the AIDS virus, LAV" Cell, 1985 40 9–17.

10. Kestler, H.W., Ringler, D.J., Mori, K., Panicali, D.L., Sehgal, P.K., Daniel, M.D., and Desrosiers, R.C. "Importance of the nef gene for maintenance of high virus loads and for development of AIDS" Cell, 1991 65 651–662.

11. Cheng-Mayer, C., Iannello, P., Shaw, K., Luciw, P.A., and Levy, J.A. "Differential effects of nef on HIV replication: implications for viral pathogenesis in the host" Science, 1989 246 1629–1632.

12. Luciw, P.A., Cheng-Mayer, C. and Levy, J.A. "Mutational analysis of the human immunodeficiency virus the orf-B region down-regulates virus replication" Proc. Natl. Acad. Sci. USA., 1987 84, 1434–1438.

13. Ahmad, N., and Venkatesan, S. "Nef protein of HIV-1 is a transcriptional repressor of HIV-1 LTR" Science, 1988 241 1481–1485.

14. Niederman, T.M., Garcia, J.V., Hastings, R.W., Luria, S., and Ratner, L. "Human immunodeficiency virus type 1 Nef protein inhibits NF-kB induction in human T cells" J. Virology, 1992 6213–6219.

15. Kim, S., Ikeuchi, K., Byrn, R., Groopman, J., and Baltimore, D. "Lack of a negative influence on viral growth by the nef gene of human immunodeficiency virus type 1" Proc. Natl. Acad. Sci. USA, 1989 86 9544–9548.

16. Dalgleish, A.G., Beverley, P.C.I., Clapham, P.R., Crawford, D.H., Greaves, M.F., and Weiss, R.A. "The CD4 (T4) antigen is an essential component of the receptor for the AIDS retrovirus" Nature, 1984 312 763–766.

17. McDougal, J.S., Mawle, A., Cort, S.P., Nicholson, J.K.A., Cross, G.D., Scheppler-Campbell, J.A., Hicks, D. and Sligh, J. "Cell tropism of the human retrovirus, HTLV-III/LAV 1. Role of T cell activation and expression of the T4 antigen" J. Immunol, 1985 135 1351–1362.

18. Horak, I.D., Gress, R.E., Lucas, P.J., Horak, E.M., Waldmann, T.A., and Boleen, J.B. (1991). "T-lymphocyte interleukin 2-dependent tyrosine protein kinase signal transduction involves the activation of p56$^{lck}$" Proc. Natl. Acad. Sci. USA., 1991 88 1996–2000.

19. Rudd, C.E. "CD4, CD8 and the TCR-CD3 complex:a novel class of protein-tyrosine kinase receptor. Immunol. Today, 1990 11 400–407.

20. Guy, B., Riviere, Y., Dott, K., Regnault, A. and Kieny, M.P. "Mutational analysis of the HIV nef protein" Virology, 1990 176 413–425.

21. Garcia, J.V. and Miller, A.D. "Serine phosphorylation-independent downregulation of cell-surface CD4 by nef" Nature, 1991 350 508–511.

22. Luria, S., Chambers, I., and Berg, P. "Expression of the type 1 human immunodeficiency virus Nef protein in T cells prevents antigen receptor-mediated induction of interleukin 2 mRNA" Proc. Natl. Acad. Sci. USA., 1991 88 5326–5330.

23. Gama Sosa, M.A., DeGasperi, R., Kim, Y-S., Fazely, F., Sharma, P. and Ruprecht, R.M. "Serine phosphorylation-independent downregulation of cell-surface CD4 by nef. AIDS Res. Human Retroviruses, 1991 7 859–860.

24. Peper, R.J., Tina, W.Z., and Mickelson, M.M. (1968). "Purification of lymphocytes and platelets by gradient centrifugation" J. Lab. Clin. Med, 1968 72 842–846.

25. Kemp, B.E., Rylatt, D.B., Bundensen, P.G., Doherty, R.R., McPhee, D.A., Stapleton, D., Cottis, L.E., Wilson, K., John, M.A., Khan, J.M., Dinh, D.P., Miles, S., and Hillyard, C.J. "Autologous red cell agglutination assay for HIV-1 antibodies: Simplified test with whole blood" Science, 1988 241 1352–1354.

26. Zhao, X., Wong, T.K., and Batten, B. "Electric mediated protein transfer into mouse oocytes" Techniques, 1989 1 37–42.

27. Kiernan, R., Marshall, J., Bowers, R., Doherty, R., and McPhee, D.A. "Kinetics of HIV-1 replication and intracellular accumulation of pathology in HTLV-1 transformed cells" AIDS Res. Human Retroviruses, 1990 6 743–742.

28. Nicholson, J.K., Spira, J.J., Aloisio, C.H., Jones, B.M., Kennedy, S., Holman, R.C., and McDougal, J.S. "Serial determination of HIV-1 titers in HIV-1 infected homosexual men: Association of rising titers with DC4 T cell depletion" AIDS Res. Human Retroviruses, 1989 5 205–215.

29. Franchini, G., and Bosch, M.L. "Genetic relatedness of the human immunodeficiency viruses type 1 and 2 (HIV-1, HIV-2) and the simian immunodeficiency virus (SIV)" Ann. N.Y. Acad. Sci., 1989 554 81–87.

30. Honda, M., Kitamura, K., Matsuda, K., Yokota, Y., Yamamoto, N., Mitsuyasu, R., Chermann, J-C., and Tokunaga, T. (1989). "Soluble IL-2 R in AIDS. Correlation of its serum level with the classificaiton of HIV-induced diseases and its characterisation" J. Immunol, 1989 12 4248–55.

31. Hattori, N., Michaels, F., Fargnoli, K., Marion, L., Gallo, R.C., and Franchini, G. "The human immunodeficiency virus type 2 vpr gene is essential for productive infection of macrophages" Proc. Natl. Acad. Sci. USA., 1990 87 8078–8084.

32. Prince. H.E., Kermani-Arab, V., and Fahey, J.L. "Depressed interleukin 2 receptor expression in acquired immune deficiency and lymphadenopathy syndromes" J. Immunol., 1984 133 1313–1317.

33. Gay, D., Maddon, P., Sekaly, R., Talle, M.A., Godfrey, M., Long, E., Goldstein, G., Chess, L., Axel, R., Kappler, J., and Marrack, P. (1987). "Functional interaction between T-cell protein CD4 and the major histocompatibility complex HLA-DR antigen" Nature, 1987 328 626–630.

34. Greene, W.C., Bohnlein, E., Siekewitz, M., and Ballard, W.B. "Structure and regulation of the human IL-2 R" Adv. Exp. Med. Biol., 1989 245 55–60.

35. Robb, R.J., Munck, A., and Smith, K.A. "T cell growth factors: Quantitation, specificity and biological relevance" J. Exp. Med., 1981 154 1455–1474.

36. Ruben, S., Poteat, H., Tan, T-H., Kawakami, K., Roeder, R., Haseltine, W., Rosen, C.A. "Cellular transcription factors and regulation of IL-2 R gene expression by HTLV-1 tax gene product" Science, 1988 241 89–92.

37. Arima, N., Kuziel, W.A., Grdina, T.A., and Greene, W.C. "IL-2-induced signal transduction involves the activation of nuclear NF-kB expression". J. Immunol., 1992 149 83–91.

38. Hurley, T.R., Luo, K., and Sefron, B. "Activators of protein kinase C induce dissociation of CD4, but not CD8, from $p56^{lck}$" Science, 1989 245 407–409.

39. Allan, J.S., Coligan, J.E., Lee, T-H., McLane, M.F., Kanki, P.J., Groopman, J.E. and Essex, M. "A new HTLV-III/LAV encoded antigen detected by antibodies from AIDS patients" Science, 1985 230 810–814.

40. Zweig, M., Samuel, K.P., Showalter, S.D., Bladen, S.V., DuBois, G.C., Lautenberger, J.A., Hodge, D.R., and Papas, T.S. "Heterogeneity of Nef proteins in cells infected with human immunodeficiency virus type 1" Virology, 1990 179 504–507.

41. Lambert, P.F., Spulholz, B.A., and Howley, P.M. "A transcriptional repressor encoded by BFV-1 shares a common carboxy-terminal domain with the E2 trasactivator" Cell, 1987 50 69–73.

42. Lillie, J.W., Loewenstein, P.M., Green, M.R., and Green, M. "Functional domains of adenovirus type 5 E1a proteins" Cell, 1987 46 1043–1046.

43. Einsbahr, K.J., Abraham, R.D. and Dick, C.J. "Protein in tyrosine phosphorilation and $p56^{lck}$ modification in human natural kilocells" J. Immunol., 1990 145 1490–1497

44. Shaw, A.S., Amrein, K.B., Hammond, C., Stern, D.F., Sefton, B.M. and Rose, J.K. "The lck tyrosine protenk inase interacts with the cytoplasmic tail of the CD4 glycoprotein through its unique amino-terminal domain". Cell, 59 627–636

45. Abrahan, R.I., Ho, S.N., McKean, D.J. "Bioassay of interleukins" J. Tiss. Cult. Methods, 1986 10 93–99

46. Minami, Y., Kono, T., Yamada, K., Kobayashi, N., Kawaliara, A., Preimutter, R.M. and Taniguchi, T. "Association of $p56^{lck}$ with IL-2 receptor β chain is critical for the IL-2 induced activation of $p56^{lck}$" EMBO J., 1993 12 759–768

47. Rudd, C.E. "CD4, CD8, and the TCR-CD3 complex: a novel class of protein tyrosine kinase receptor" Immunol. Today, 1990 11 400–405

48. Irving, S.G., June, C.H., Zippel, P.F., Siebenlist, U. and Kelly, K. "Mitogen-induced genes are subect to multiple pathways of regulation in the initial stages of T-cell activation" Mol. Cell Biol., 1989 9 1034–1040

49. Siu, G., Wurster, A.L., Lipsick, J.S. and Hedrick, S.M. "Expression of the CD4 gene requires a myb transcription factor" Mol. Cell Biol., 1992 12 1592–1604

50. Harris, M. and Coates, K. "Identification of cellular proteins that bind to the human immunodeficiency virus type 1 nef gene product in vitro: a role for myristoylation" J. Gen. Virol., 1993 74 1581–1589

51. Barber, E.K., Dasgupta, J.D., Schlossman, S.F., Trevillyan, J.M. and Rudd, D.E. "The CD4 and CD8 antigens are coupled to protein-tyrosine kinase ($p56^{lck}$) that phosphorylates the CD3 complex" Proc. Natl. Acad. Sci. USA, 1989 86 3277–3281

52. Collins, T.L. et al "$p56^{lck}$ association with CD4 is required for the interaction between CD4 and the TCR/CD3 complex and for optimal antigen stimulation" J. Immunology, 1992 148 2159–2162

53. Werner, T., Ferroni, S., Saermark, T., Brack-Werner, R., Banati, R.B., Mager, R., Steinaa, L., Kreutzberg, G.W. and Erfle, V. "HIV-1 Nef protein exhibits structural and functional similarity to scorpion peptides interacting with $K^+$ channels" AIDS, 1991 5 1301–1308

54. Azad, A.A., Failla, P., Lucantoni, A., Bentley, J., Mardon, C., Wolfe, A., Fuller, K., Hewish, D., Sengupta, S. Sandkovich, S., Grgacic, E., McPhee, D. and Macreadie, I.G. "Large scale production and characterisation of recombinant human immunodeficiency virus type 1 Nef" J. Gen. Virology, 1994 75 651–655

What is claimed is:

1. A method of screening compounds for activity as analogues or antagonists of $Nef_{2-19}$ peptide, comprising measuring the effectiveness of a test compound in an assay of a biological activity of $Nef_{2-19}$ peptide selected from the group consisting of membrane perturbation, down-regulation of CD4 expression, down-regulation of IL-2 receptor expression, inhibition of $p56^{lck}$ phosphorylation, and binding of $Nef_{2-19}$ to $p56^{lck}$.

2. A method according to claim 1, comprising the step of assaying the effect of a test compound on the ability of $Nef_{2-19}$ peptide to inhibit phosphorylation of $p56^{lck}$ in peripheral blood mononuclear cells in response to stimulation with IL-2.

3. A method according to claim 1, comprising the step of assaying the effect of a test compound or the ability of $Nef_{2-19}$ peptide to bind directly or indirectly to $p56^{lck}$.

* * * * *